US006979566B2

(12) United States Patent

Friedman et al.

(10) Patent No.: US 6,979,566 B2

(45) Date of Patent: Dec. 27, 2005

(54) METHOD OF TREATMENT OF VIRAL INFECTION INCLUDING HIV USING WATER SOLUBLE FULLERENES—III

(75) Inventors: Simon H. Friedman, San Francisco, CA (US); Raymond F. Schinazi, Decatur, GA (US); Fred Wudl, Santa Barbara, CA (US); Craig L. Hill, Atlanta, GA (US); Diane L. DeCamp, Atlanta, GA (US); Rintje P. Sijbesma, Eindhoven (NL); George L. Kenyon, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/355,365

(22) Filed: Feb. 1, 2003

(65) Prior Publication Data

US 2004/0044062 A1 Mar. 4, 2004

Related U.S. Application Data

(63) Continuation of application No. 09/771,082, filed on Jan. 25, 2001, now Pat. No. 6,613,771, which is a continuation of application No. 09/246,011, filed on Sep. 21, 1998, now Pat. No. 6,204,391, which is a continuation of application No. 08/184,992, filed on Jan. 24, 1994, now Pat. No. 5,811,460.

(51) Int. Cl.[7] .............................................. C07C 229/37

(52) U.S. Cl. ....................... 435/219; 435/236; 546/186; 548/338.1; 560/101; 562/441; 562/442; 562/488; 564/155; 564/308; 564/322; 564/378

(58) Field of Search ................................. 435/219, 236; 546/186; 548/338.1; 560/101; 562/441, 442, 488; 564/155, 308, 322, 378

(56) References Cited

U.S. PATENT DOCUMENTS

| | | | | |
|---|---|---|---|---|
| 5,811,460 A | * | 9/1998 | Friedman et al. | 514/563 |
| 6,204,391 B1 | * | 3/2001 | Friedman et al. | 548/338.1 |
| 6,613,771 B2 | * | 9/2003 | Friedman et al. | 514/256 |

* cited by examiner

*Primary Examiner*—Richard L. Raymond

(74) *Attorney, Agent, or Firm*—Peters, Verny, Jones, Schmitt & Aston, LLP; Howard M. Peters

(57) ABSTRACT

A water soluble derivative of buckministerfullerene ($C_{50}$) having antiviral and virucidal properties is used to inhibit human retroviral replication and infections. The derivatized fullerene is symmetrically substituted with polar organic moieties containing 1 to 20 carbon atoms and optionally further containing oxygen or nitrogen.

15 Claims, 9 Drawing Sheets

(1 of 9 Drawing Sheet(s) Filed in Color)

1, X = $HOC(O)(CH_2)_2C(O)NH(CH_2)_2$-

METHOD OF TREATMENT OF VIRAL INFECTION INCLUDING HIV USING WATER SOLUBLE FULLERENES— III

Related Applications

This application is a continuation of U.S. Ser. No. 09/771,082, filed Jan. 25, 2001, now U.S. Pat. No. 6,613,771, which is a continuation of U.S. Ser. No. 09/246,011 filed Sep. 21, 1998, now U.S. Pat. No. 6,204,391, which is a continuation of U.S. Ser. No. 08/184,992 filed Jan. 24, 1994 now U.S. Pat. No. 5,811,460.

This work was supported by U.S. Government grants: NIGMS grant GM39552 and NSF grant DMR9111097; Department of Veterans Affairs and U.S. Public Health Service grants Al 32903 and Al 25899; National Science Foundation grants DMR-88-20933, DMR-91-11097, and CHE 89-08323; and, NIH AIDS Research and Reference Program grant Nos. HIV-1 G9106 and HIV 1H1122. The U.S. Government may have rights in this invention.

BACKGROUND OF THE INVENTION

1. Field of the Invention

This invention relates to compounds used for chemotherapeutic treatment of infections produced by human retroviruses and to methods for their use in treatment of such diseases as acquired immunodeficiency syndrome, AIDS, or AIDS-Related Complex (ARC).

2. Description of Related Art

There have been more than 100,000 deaths from AIDS and ARC to date, yet currently no treatments for the diseases effect cures. The drugs AZT, DDI and DDC have been approved by the Food and Drug Administration, and when used alone or in combination prolong the life of patients, but do not produce cures. Approximately seventy additional compounds are in the early stages of clinical testing, but FDA approval for additional compounds has not been forthcoming.

Many of the presently known compounds are toxic and may be eliminated in humans rapidly, requiring heavy dosage schedules. In addition, most nucleoside analogs, such as AZT, require initial phosphorylation by cellular kinases for activation.

An especially promising target for treatment and prevention of AIDS and ARC is the HIV protease. HIV produces a small, dimeric aspartyl protease which specifically cleaves the polyprotein precursors encoding the structural proteins and enzymes of the virus. This proteolytic activity is absolutely required for the production of mature, infectious virions and is therefore an attractive target for therapeutic intervention. The resolved X-ray crystallographic structures of HIV-1 protease and a handful of HIV-1 protease-inhibitor complexes are available. The active site of this enzyme can be roughly described as an open-ended cylinder which is lined almost exclusively by hydrophobic amino acids (FIG. 1A). Notable exceptions to this hydrophobic trend are the two catalytic aspartic acids (Asp25, Asp125), which catalyze the attack of water on the scissile peptide bond of the substrate. Efforts in molecular genetics, protein biochemistry, enzymology, medical chemistry, virology, X-ray crystallography, molecular modeling have all been marshalled to identify specific inhibitors of this critical viral enzyme (C. Debouck, *AIDS Res. and Human Retroviruses*, 8:153–164, 1992). Some of these compounds have also demonstrated activity in humans infected with HIV-1, as measured by p24 decline and increased $CD4^+$ cell counts.

The research on buckminsterfullerene ($C_{60}$) and other fullerenes in the last few years has been extraordinary. Fullerenes are hollow molecules composed of pure carbon atoms. Typically, fullerenes each have 12 pentagons, but differing numbers of hexagons. The pentagons are required in order to allow curvature and eventual closure of the surface upon itself. The most abundant species to date is the $C_{60}$ molecule known as buckminsterfullerene. Its crystal and molecular structure have been resolved using single-crystal x-ray diffraction methods (S. Liu, et al., *Science*, 254:408–410, 1991). $C_{60}$ consists of 12 pentagons and 20 hexagons and is classified as an icosahedron, the highest symmetry structure possible.

Naturally occurring fullerenes have recently been found in the geological environment of Shunga, a town in the lake region of Karwelia in Russia (P. R. Buseck, et al, *Science*, 247:215–217, 1992). Synthetic fullerenes are produced by high temperature vaporization of solid graphite rods by resistive heating or arc heating in the presence of a few to several torr of rare gas. The soot produced by the vaporization contains varying levels of fullerenes, depending on the vaporization conditions. However, the majority of the fullerenes produced are $C_{60}$ and $C_{70}$, with $C_{60}$ being more abundant. The fullerenes are extracted from the soot by placing the soot into a solvent in which the fullerenes are soluble. The solution is then filtered and allowed to evaporate to yield fullerene powders. Alternatively, the fullerenes can be purchased commercially.

A host of physical and chemical properties of these materials have now been established, and their potential applications in several areas are now apparent. To date, however, no specifically targeted fullerene molecule, with a special biological function in mind, has been prepared. There exist a variety of procedures for functionalization of $C_{60}$ fullerenes. (See, for example, *Fullerenes Synthesis, Properties, and Chemistry of Large Carbon Clusters*, G. Hammond, et al., Eds., ACS Symposium Series 481, American Chemical Society, Washington, D.C., 1992; see entire issue No. 3 of *Acc. Chem. Res*., 25, 1992; A. Hirsch, et al., *Chem. Int. Ed. Engl*., 31, 766, 1992). Nearly all the fullerenes characterized are nonderivatized homologs (spheroids, tubes, etc.) of $C_{60}$, and like $C_{60}$ itself, are highly hydrophobic and insoluble in aqueous media. Recently fullerene-cyclodextrin inclusion compounds comprising $C_{60}$ embedded in γ-cyclodextrin (T. Anderson, et al., *J. Chem. Soc. Chem. Commun*., 1992:604–606, 1992) and fullerenes containing multiple covalently attached substituents (U.S. Pat. No. 5,177,248) or multiple covalently attached amine-derived substituents (A. Hirsch, et al., *Angew. Chem. Int. Ed. Engl*., 30:1309–1310, 1991; V. Mehrotra, et al., *Chem. Mat*, 4:20–22, 1992) have been shown to have water solubility, but the lability of the former, and the configurational dynamism and complex isomerism of the latter compounds would preclude a ready and unequivocal evaluation of structure-activity data in biological systems. Polyhydroxylated, water-soluble fullerenes have also been prepared, but no single, fully characterized isomer has been isolated to date (L Y. Chiang, et al., *J. Chem. Soc. Chem. Commun*., 1992:1701–1793, 1992).

The need exists, therefore, for therapeutic compounds useful in ameliorating or preventing retroviral infections, especially AIDS and AIDS-Related Complex (ARC). The present invention provides derivatives of $C_{60}$ that are water soluble at physiologic conditions and both prophylatically and therapeutically effective against the virus that causes AIDS and ARC.

SUMMARY OF THE INVENTION

The ability of water soluble buckminsterfullerene ($C_{60}$) derivatives to inactivate virus through binding with the active site of HIV-1 protease (HIVP) and/or inhibition of reverse transcriptase has been examined through model building and simple physical chemical analysis. The prediction that these compounds should bind to the active site of the HIVP protease, and thereby act as inhibitors, has been borne out by assay of cells acutely and chronically infected with human immunodeficiency virus (HIV).

The complexes generated via computer models suggest that the virucidal activity of $C_{60}$ derivatives results from a snug fit of the fullerene into the active site of the HIVP protease, thereby removing at least 298 $Å^2$ of primarily nonpolar surface from solvent exposure and driving ligand/protein association. A method for screening the binding of candidate buckministerfullerene derivatives with the active site of HIVP using computer simulation is also provided.

Kinetic analysis of HIVP in the presence of a water-soluble $C_{60}$ derivative, bis(phenethylamino-succinate), suggests a competitive mode of inhibition. This is consistent with and supports the predicted binding mode.

The water soluble $C_{60}$ derivatives for inactivating HIV by interacting with HIV by Van der Waals contacts with the nonpolar HIVP surface, are substituted symmetrically with organic moieties comprising from 1 to about 20 carbon atoms each and optionally further comprising polar heteroatoms, such as oxygen and nitrogen. The preferred fullerene derivatives are diamino derivatives synthesized in three steps from $C_{60}$ via a suitably substituted diphenyldiazomethane. High-resolution mass spectrometric analysis of these compounds is possible only under the mild conditions of matrix-assisted laser desorption/ionization Fourier transform mass spectrometry. Direct infrared or ultraviolet laser desorption degrades the compounds so that only $C_{60}$ ions are observed, in either positive or negative mode. Virus inactivation assays are provided for confirming activity of the $C_{60}$ derivatives against human immunodeficiency virus type 1 (HIV-1) and HIV-2. Inhibition of acutely and chronically HIV-1 infected human peripheral blood mononuclear cells (PBMC) and chronically infected lymphocytes (e.g., H9 cells) by the preferred water soluble bis(monosuccinimide) derivative of p,p'-bis(2-aminoethyl)-diphenyl has an $EC_{50}$ at a concentration of 7 $\mu$M, and no cytotoxicity is shown in uninfected PBMC as well as other cell lines. Inhibition of protease (HIVP) and reverse transcriptase (HIVRT) is also shown.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 shows photographs of computer simulations of the HIV-1 protease.

FIG. 6 shows a schematic representation of the DOCK3 complex of compound 2 with the HIVP.

FIG. 9 shows graphs of mass molecular ion measurements of 2c.

A DETAILED DESCRIPTION OF THE INVENTION

Figure 1A:
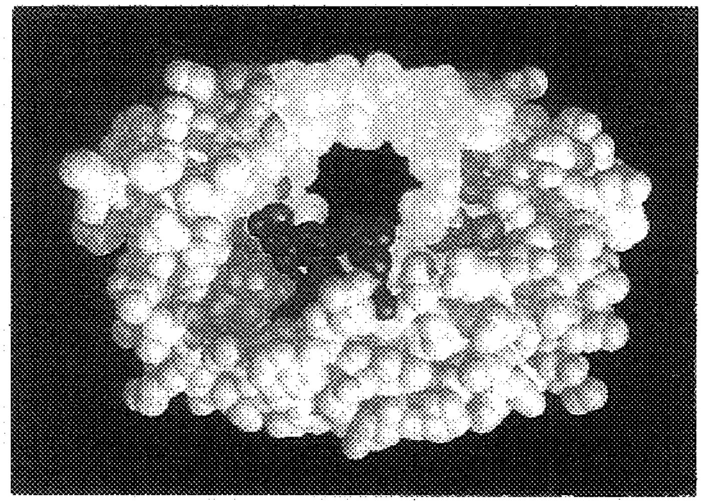
FIG. 1A shows a "Front" view of the HIV-1 protease. Color coding is as follows: Yellow: Leu, Ile, Phe, Tyr, Val, Trp, Pro, Gly, Ala. Blue: Lys, Arg. Red: Asp, Glu. Cyan: Thr, Ser, Gln, Asn, Cys, Met, His. Gray: regions greater than 10 Å from the center of the active site.

Provided herein are derivatives of buckminsterfullerene ($C_{60}$) that are water soluble at physiologic conditions and have virucidal activity, especially against the viruses causing AIDS and ARC in humans. The fullerene derivatives of this invention inactivate the protease specific to the human immunodeficiency virus 1 ("HIVP"). HIVP is characterized by an active site in the form of a cylinder or "tunnel" lined almost exclusively by hydrophobic amino acids (as shown in FIG. 1A) with an interior diameter of about 10 Å. Contained within the active site are two anionic residues, $Asp_{25}$ and $Asp_{125}$. A $C_{60}$ molecule (a fullerene) has an external diameter of 10 Å, approximately the same radius as the cylinder that describes the active site of the HIVP. Since $C_{60}$ and its derivatives are primarily hydrophobic, it has been discovered herein that a strong hydrophobic interaction exists between the $C_{60}$ derivative and the active site surfaces of the HIVP protease sufficient to block or partially block the catalytic aspartates at the enzymatic active site. This interaction with the protease that activates HIVP makes $C_{60}$ derivatives inhibitors of the HIVP. This interaction is further increased if the $C_{60}$ is substituted on its surface with polar substituents symmetrically situated around a central axis. The polar substituents can be any alkyl or aryl-alkyl substituent, particularly those substituted with nitrogen and oxygen, containing from one to about 20 carbon atoms. These polar substituents are selected and oriented with respect to the $C_{60}$ molecule so that, upon binding of the derivative with the active site of HIVP, the polar substituents generally extend from the $C_{60}$ along or through the mouth of the cylinder that describes the active site of the HIVP so as to be in contact with the solution.

Additional non-limiting examples of the water-soluble $C_{60}$ derivatives useful in the practice of this invention are shown in Table 1
TABLE 1
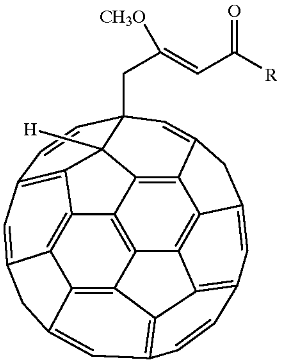
a.
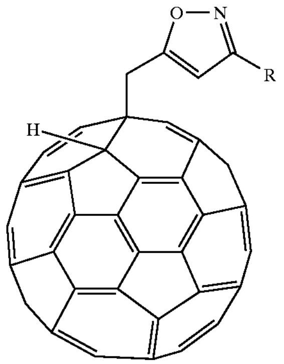
b.
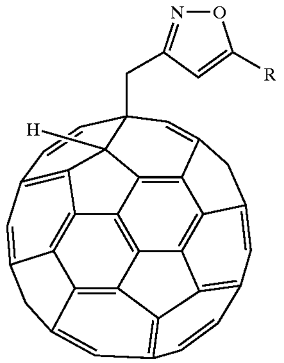
c.
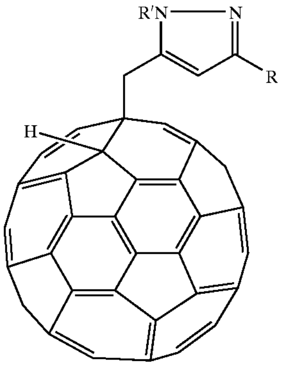
TABLE 1-continued
d.
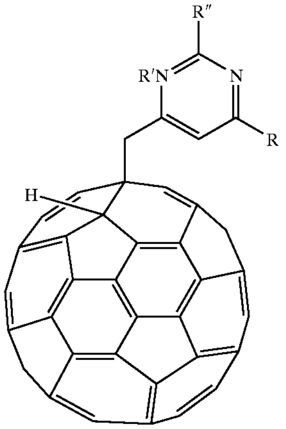
e.
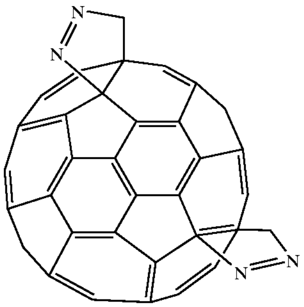
f.
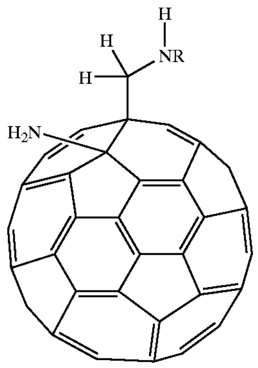
g.
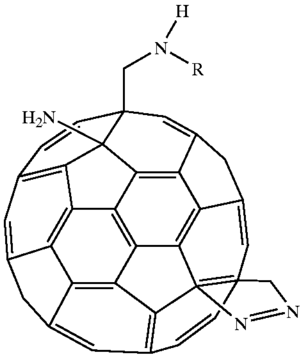
h.

TABLE 1-continued

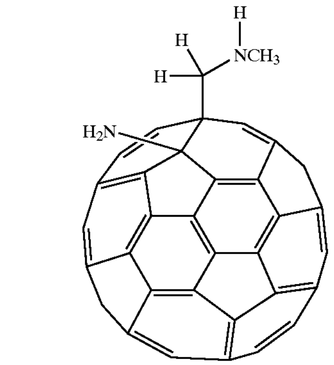

i.

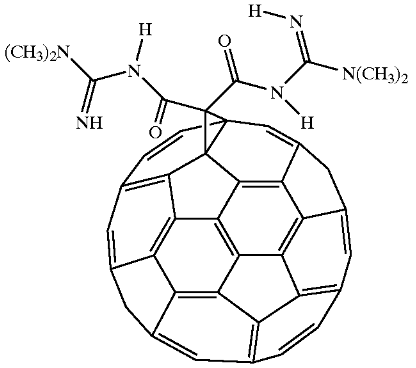

j.

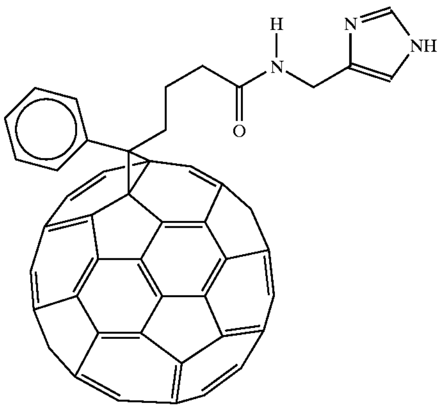

k.

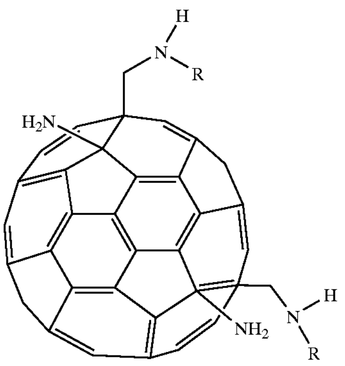

l.

TABLE 1-continued

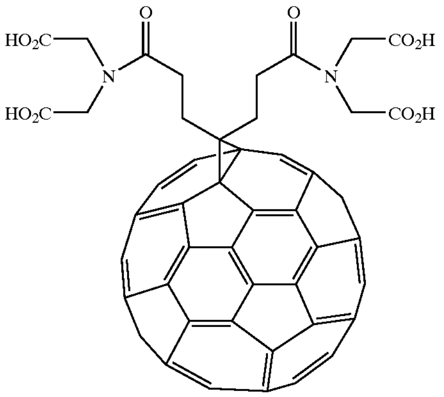

m.

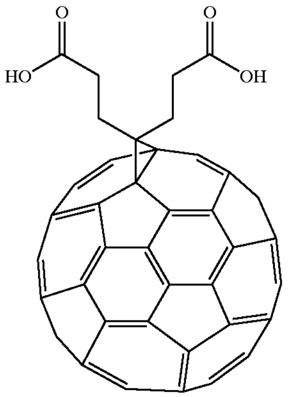

n.

The advantages of $C_{60}$ derivatives for blocking the active site of HIVP over those known in the art are twofold. First of all, the $C_{60}$ derivatives of this invention represent nonpeptide-based compounds that, through careful modeling, result in effective, tightly binding HIVP inhibitors. Second, the buckminsterfullerenes present a rigid, conformationally restricted scaffold upon which to mount nonpolar chemical moieties for establishing a hydrophobic interaction between the nonpolar active site surface of HIVP and the $C_{60}$ surface. Because of the steric bulk of $C_{60}$ and its complementarity to the active site surface, there are severe limitations to the orientations it can adopt within the active site. Essentially, the principal degree of freedom of a $C_{60}$ derivative of this invention within the active site is rotation around the central axis of symmetry. All of these attributes simplify the problem of predicting the binding modes of various derivatives.

The $C_{60}$ derivatives of this invention are soluble in water, being solubilized by attachment of polar substituents, including ionic groups, situated in a well-defined position on the surface of the fullerene. That is, it is preferred that the compounds be substituted with substituents symmetrically located, isometrically pure, and configurationally stable covalently derivatized fullerenes. As the term “symmetrical” is used herein the substituents need not be identical to be symmetrically located. As used herein derivatives of buckminsterfullerenes that contain a functionalizable carbon atom are referred to as “fulleroids.” As used herein, “methanofullerene is a fulleroid having a closed cyclopropane ring rather than an annulene (ring-opened fulleroid) structure.

The synthetic methodology presented herein provides a method for facilely and specifically modifying the $C_{60}$ surface to obtain water soluble, isomerically pure, symmetrical $C_{60}$ derivatives with virucidal and antiviral properties against HIV. As used herein, the term "virucidal" shall mean that the compound acts outside cells to prevent binding to a receptor. As used herein, the term "antiviral" shall mean that the compound is effective intracellularly to inhibit or kill virus. Among the various methods available for functionalization of $C_{60}$, the method of cyclo addition is by far the simplest and most versatile. Therefore, in one embodiment of the invention, the fulleroids are methanofullerenes derived from diphenyldiazomethane since synthesis of the precursor benzophenone derivatives is generally facile. An example of the reaction scheme for production of a methanofullerene derivatized $C_{60}$ compound that is water soluble at physiologic conditions is according to Scheme I.

Scheme I

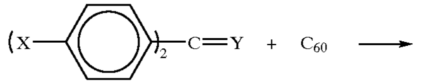

1a, X = $CH_3C(O)NH(CH_2)_2$
Y = O
1b, X = $CH_3C(O)NH(CH_2)_2$
Y = $NNH_2$
1c, X = $CH_3C(O)NH(CH_2)_2$
Y = $N^{(+)} = N^{(-)}$

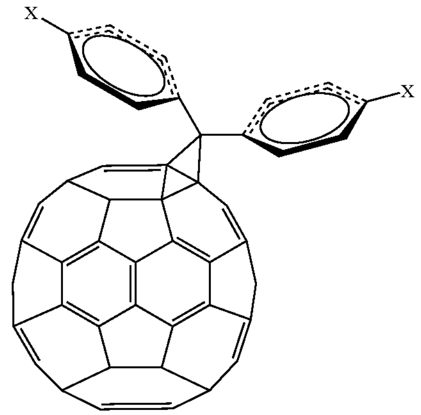

2a, X = $CH_3C(O)NH(CH_2)_2$
2b, X = $(CH_2)_2NH_2$
2c, X = $HOC(O)(CH_2)_2C(O)NH(CH_2)_2$

An example of a reaction scheme for production of an annulene derivatized $C_{60}$ compound that is water soluble at physiologic conditions is according to Scheme II.

Scheme II

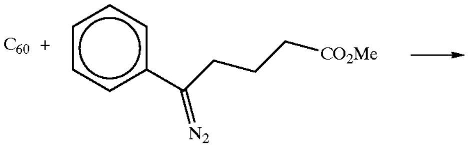

-continued

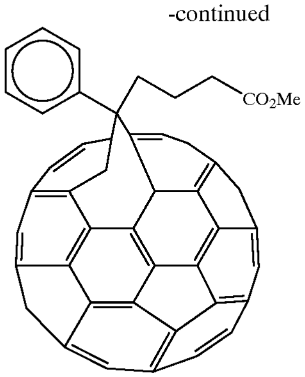

+ Trace Cyclopropane

The x-ray crystal structure of HIVP is well known and the three-dimensional coordinates are available in standard Brookhaven database format from Protein DataBank, file 3hvp. Computer models based upon the known three-dimensional coordinates of HIVP and $C_{60}$ can be utilized to develop compounds having the physical attributes required by this invention that bind tightly to HIVP, preferably to the active site of HIVP. Programs suitable for generating predicted three-dimensional structures from two-dimensional data, include: SYBYL (Version 5.4) and Concord (Tripos Associates, St. Louis, Mo.), 3-D Builder (Chemical Design Ltd., Oxford, U.K), CataLyst (Bio-CAD Corp., Mountain View, Calif.), Daylight (Abbott Laboratories, Abbott Park, Ill.) and MINDOCK and DOCK3 (E. C. Meng, *J. Comp. Chem.*, 13:505–524, 1992. The program is available through University of California, San Francisco). To model complementarity, docking, and binding of test complexes of $C_{60}$ and HIVP, computer simulations were generated via the program DOCK3 using the method described in Example 1. The surface that is desolvated due to complex formation between these compounds is shown to be almost exclusively hydrophobic. In addition, kinetic analysis supports a competitive mode of inhibition of a tested $C_{60}$ derivative, consistent with the computer models of complexes generated.

In general, the goal of structure based inhibitor design is to design a molecule that is 1) complementary in shape to the active site of the target and 2) has surfaces that are chemically appropriate to the active site surfaces. As used herein the term "chemically appropriate" means that (a) non-polar inhibitor surfaces are in contact with non-polar proteins surfaces leading to association driven by hydrophobic effect, (b) hydrogen bond donating species are in contact with hydrogen bond accepting species and (c) positively charged species are in contact with negatively charged species.

Preferably the programs DOCK3 and MINDOCK are used to generate complexes of modeled inhibitors with the active site of the HIVP to determine chemically appropriate protease inhibitor compounds, although one skilled in the art will understand that alternative methods can be used. Because of subtleties in the energetics of binding, the potential strength of binding is approximated by examining the types of surfaces that are brought into contact upon formation of the complex. The HIVP active site surface is dominated by non-polar amino acids. Appropriateness of fullerene compounds in binding to the HIVP is based on the non-polar surface of the fullerene interacting with these HIVP surfaces. In model complexes, this type of surface desolvation accounts for <90% of the surface desolvated.

From simple model systems the strength of binding is known to depend upon this type of nonpolar surface desolvation and this is the major interaction for nonpolar fullerene derivatives. Therefore, an estimation of binding strength can be made from calculating the amount of surface desolvated by formation of a complex between a fullerene and the HIVP.

The method for computing the desolvation energy released upon formation of an inhibitor/HIVP complex comprises the following steps:

1. Prepare the Atomic Resolution Structure of the HIVP;

In general the uncomplexed, or "open" structure of the HIVP (Brookhaven protein data bank #3hvp) is used for modeling, since this structure more nearly approximates the ground-state conformation of the HIVP. Therefore, as a first approximation, its conformational energy can be ignored in the evaluation of binding free energy. Utilizing the associated programs of DOCK3, gridded representations of the active site and surrounding portions of the HIVP are generated. Each grid point contains information as to the Van der Waals surface parameter as well as the electrostatic potential at that point. This gridded values are later utilized by DOCK3 to score the energies of the orientations of inhibitors generated.

2. Model the Structure of the Hypothetical Inhibitor;

The hypothetical structure is drawn up using the SYBYL package. If any conformational flexibility is present in the molecule, lowest energy conformations are initially set, and the molecule is then minimized. Electrostatics for the molecule are generated using the Gasteiger-Huckel option. The molecule is then saved in the .mol2 format that DOCK3 and MINDOCK require.

3. Fit the Model of the Inhibitor into the Active Site of the HIVP Model Using the Programs DOCK3 and MINDOCK;

The inhibitor structure is fitted into the active site using either DOCK3 or MINDOCK Using the Single Mode, each program generates literally thousands of orientations of the inhibitors within the active site of the HIVP, which are evaluated by the program for reasonable Van der Waals contacts and complementary electrostatics. The main difference between DOCK3 and MINDOCK is that the latter does a rigid-body minimization of the inhibitor with respect to the HIVP as an additional step after each orientation so that a more efficient search of the space in the active site can be effected. Summation of all of the Van der Waals and electrostatic interactions results in an energy score used to rank the top conformations.

4. Generate Molecular Surfaces for the Inhibitor, the HIVP, and for the Inhibitor/HIVP Complex;

The energy score generated by the computer program must be adjusted to arrive at the binding energy because several components of binding free energy are not taken into account. The first such factor is salvation effects. Electrostatic interactions are significantly muted when they take place in aqueous solution due to the energy cost of desolvating the charged species that are interacting. For example, attraction of a positive charge and a negative charge is decreased approximately 20 fold in water solution as compared with in a vacuum. A second important salvation effect is the hydrophobic effect, the tendency for non-polar, uncharged species to bind to each other in aqueous solution. This effect is thought to be caused by a restructuring of water as it comes into contact with non-polar surfaces. Due to the hydrophobic effect, the strength of interaction of uncharged, non-polar species in water is underestimated by simply calculating the Van der Waals interactions between them.

However, an accurate estimate of the contribution of the hydrophobic effect to ligand/protein affinity is based on the surface area of non-polar atoms removed from water contact upon complex formation. The second factor is translational/rotational entropy, which is roughly a fixed energy cost paid when two freely moving species associate, thereby eliminating 3 degrees of translational and 3 degrees of rotational freedom.

These complicating factors can be simplified in analysis of fullerene inhibitors of the HIVP because the active site surfaces of HIVP are predominantly nonpolar, as are the surfaces of derivatized fullerenes of this invention. In typical model complexes of fullerene derivatives, <90% of the surfaces that are desolvated upon complex formation are non-polar carbon surfaces. Therefore, the binding energy (which is related to the affinity of binding) can be estimated by looking at how non-polar surface desolvation in simple model systems affects binding energy.

Molecular surfaces are calculated by the program MS, which is a part of the MIDAS molecular display package. These can then be broken down and analyzed.

5. Break Down the Surfaces Transferred According to Atom Type (e.g. carbon, nitrogen or oxygen);

6. Determine the Change in Surface Area Upon Complexation According to Atom Type from the Surfaces Generated in Step 4;

The change in molecular surface upon complex formation is determined by subtracting the sum of the areas of fully solvated HIVP and inhibitor from the area of the complex. In order to determine how much of this desolvated surface is non-polar, the contribution from each discrete element of the surface is summed according to atom type (e.g., carbon—non-polar; oxygen and nitrogen—polar). This sum is a value representing the amount of non-polar surface desolvated upon complexation, which may then be used to estimate binding energy, and therefore inhibitor affinity.

7. Estimate the Change in Binding Energy that Should Accompany the Desolvation of Inhibitor and HIVP Surfaces Upon Complexation;

Recent work by Tunon, et al. (*Protein Eng*., 5:715–716, 1992) has shown that each square Angstrom of desolvated non-polar molecular surface area is equivalent to about 70 cal/mol of binding energy. This value is therefore used to convert the non-polar surface determined in steps 5 and 6 into a binding energy contribution.

8. Use These Energies to Estimate the Binding Constant or Affinity of the Inhibitor with the HIVP.

Because of complicating factors, including the issue of rotational/translational entropy described above, the binding energy is best understood as relative to that of a known compound, to estimate the improvement in binding in comparison to the known compound. Therefore, the change in non-polar surface desolvation is measured relative to the change that occurs with a compound that has a known binding affinity. The increase in binding energy calculated above is then taken as the potential improvement in binding of the unknown compound relative to the known compound.

The model of underivatized $C_{60}$ demonstrates the potential for $C_{60}$-based inhibitors of the HIVP. The main driving force behind the association of the HIVP and the fullerene derivative examined is a presumably hydrophobic interaction between the nonpolar active site surface of HIVP and the $C_{60}$ surface. Upon formation of the $C_{60}$-HIVP complex, about 298 $Å^2$ of primarily hydrophobic surface area is removed from solvent exposure, resulting in a free energy release of about 7–11 kcal/mol. In addition there is an opportunity for increasing binding energy by the introduction of specific interactions. One mode of electrostatic interaction is a salt bridge between the catalytic aspartates on the floor of the active site and a cationic site on the $C_{60}$ surface. It is known that several dicationic metals, such as $Cu^{++}$ are effective inhibitors of the HIVP (T. C. Woon, et al., *Int. J. Biochem.*, 24:911–914, 1992; Z. Y. Zhang, et al., *Biochemistry*, 30:8717–8721, 1991). The $K_i$ values for divalent cations with the HIVP active site are in the micromolar range, corresponding to ≈8 kcal/mol loss of binding energy, over and above the Gibbs energy loss, due to freezing out translational entropy. It has been shown that introduction of a single amine/carboxylate salt bridge can increase the binding energy of a ligand to its receptor by ≈4 kcal/mol (D. Santi, et al., *J. Med. Chem.*, 16:273–280, 1973). Thus, incorporation of even a fraction of the binding energy due to this type of interaction into a $C_{60}$ derivative results in an improvement in binding energy over the $C_{60}$ core binding energy of several orders of magnitude. Therefore, in one embodiment of this invention the $C_{60}$ derivative incorporates polar substituents that provide a cation site such that a salt bridge can form between the enzymatic aspartates in the active site and the $C_{60}$ derivative, providing a tight electrostatic interaction therebetween. For instance, direct amino adducts of $C_{60}$ (A. Hirsch, et al., supra) increase the electrostatic interaction. However, the stoichiometry of the synthesis of direct amine adducts is hard to control and does not predictably result in symmetrical molecules. Hence, these derivatives are not preferred.

Synthesis of the preferred symmetrical, isometrically pure, and water soluble buckminsterfullerenes of this invention, which incorporate moieties necessary to solubilize the molecule at physiologic conditions of pH and orient the $C_{60}$ with respect to the active site of HIVP, can be generally carried out as follows. The substituted diphenyldiazomethane is prepared in the known manner from the substituted benzophenone hydrazone by oxidation with nickel peroxide. The formation of intermediate 2a from buckminsterfullerene $C_{60}$ follows the methanofullerene synthesis method (T. Suzuki, et al., *Acc. Chem. Res.*, 25:157, 1992). The bis(acetamide) is preferably hydrolyzed in acetic acid/aqueous hydrochloric acid and converted to bis (succinamide) 2c by treatment with succinic anhydride. Compounds 2a–c exhibit the usual methanofullerene properties. Compound 2c is soluble in water at pH≧7, making it an ideal substrate for evaluation of physiological and pharmaceutical properties of a methanofullerene. A more detailed description of the synthesis and characterization of a sample methanofullerene compound appears in EXAMPLE 5. The difficult step in the synthesis of these compounds is the hydrolysis of bis(acetamide) 2a intermediate, which we found to be extremely sluggish, requiring workup after about 16 hours, followed by repeated submission of the unreacted 2a to hydrolytic conditions. Many different combinations of solvents and acids were tried to determine optimal conditions as described in EXAMPLE 5e below.

The water solubility of the $C_{60}$ derivatives at physiologic pH, generally in the range between pH 6 and 8, is not predictable. For instance, sulphone derivatives tested form micellar aggregates and precipitate in this pH range. Also the hydrochloride salt of compound 2b is found not to be soluble. Surprisingly, however, the tosylate salt is water-soluble. This is a counterintuitive result since salts wherein both ions are large usually are water-insoluble and salts of large cations with small anions (and vice versa) are more water-soluble. In addition, the N,N,N',N' tetramethyl derivative of 2b hydrochloride is also insoluble in water. Finally, reaction of the N,N,N',N' tetramethyl derivative with propane sultone affords a zwitterion which is also insoluble in water. To overcome these negative results, 2b was reacted with succinic anhydride, yielding 2c. The bis sodium salt was sparingly soluble in water (about 1 mg/mL) and has been found to inhibit (HIVRT).

Thus, compound 2b is a key intermediate for obtaining the methanofullerene $C_{60}$ water soluble derivatives of this invention. Further derivatization to produce additional water-soluble cationic derivatives of $C_{60}$ having the necessary physical parameters and characteristics to specifically inhibit HIVP can be made by one skilled in the art using known methods for derivatizing the fullerenes. Structural characterization using infrared, UV-vis, and $^1H$ NMR spectra of the synthetic compound is used to confirm the structure of the compound of interest. For example, the structure of synthetic 2b was confirmed by infrared, UV-vis, and $^1H$ NMR spectra as described in EXAMPLE 6 to be in good agreement with the proposed structure. The resonances of the bridgehead carbons for methanofullerenes are in the 77–80 ppm region; while those of the fulleroids are in the 137–150 ppm region (M. Prato, et al., *J. Am. Chem. Soc.*, 115:8479–8480, 1993). The $^{13}C$ NMR resonance of the bridgehead atoms of 2b appeared at 79.37 ppm. Based on this fact and the UV-vis spectra of 2a–c all exhibiting the diagnostic 430-nm peak of methanofullerenes (Prato, supra), the 2b compound was assigned the methanofullerene structure shown in scheme I.

Because the quantities available for analysis are often too small for traditional elemental analysis, mass spectrometry is preferably used for assessment of elemental composition. Several attempts at fast atom bombardment mass spectrometry (FABMS) failed to produce spectra with a molecular ion peak; the only observable peaks were due to $C_{60}$. Similarly, direct laser desorption Fourier transform mass spectrometry (FTMS), using either pulsed carbon dioxide laser desorption (C. L Wilkins, et al., *Anal. Chem.*, 57:520-524, 1985) or ultraviolet laser desorption, yielded spectra containing only peaks due to $C_{60}^+$ ions. However, the somewhat gentler technique of matrix-assisted laser desorption as described in Examples 6 and 7 did provide the requisite analytical information. From the mass spectral experiments, it is clear that methanofullerene derivatives are readily converted to $C_{60}$ under FABMS or direct laser desorption conditions, but that use of MALDI-FTMS can suppress this undesired decomposition and provide analytical data on the unchanged analyte. Thus, it is extremely important to use the appropriate mass spectral technique if reliable conclusions are to be drawn regarding structures of putative fulleroids and methanofullerenes.

The therapeutic and prophylactic efficacy of the compounds of this invention has been shown by in vitro assays. The bis(monosuccinimide) derivative of p,p'-bis(2-aminoethyl)diphenyl-$C_{60}$ (compound 2c), prepared by the fulleroid route, is active against human immunodeficiency virus type 1 (HIV-1) and HIV-2 (50% effective concentration [$EC_{50}$] averaging ≈6 μM) in acute or chronically infected human lymphocytes and is active in vitro against 3'-azido-3'-deoxythymidine-resistant HIV-1 ($EC_{50}$ 3 μM). The virucidal properties of compound 2c were confirmed by virus inactivation assays. Compound 2c was noncytotoxic up to 100 μM in peripheral blood mononuclear cells and H9, Vero, and CEM cells. In cell-free assays, compound 2c showed comparable activity against HIV-1 reverse transcriptase and DNA polymerase a (50% inhibitory concentration of ≈5 μM). Activity against HIV-1 protease, however, was selective.

Thus, the water-soluble fullerenes of this invention have selective activity against HIV-1 in acutely and chronically infected cells. Compound 2c was also shown to have virucidal properties, suggesting direct interactions between the fullerene and HIV-1. The virucidal properties of this compound probably account for the major viral inhibitory activity observed in vitro. Although the mechanism of antiviral action of this compound is not yet known, our results as shown in TABLE 2 suggest that the compound inhibits HIV-1 RT and DNA polymerase a and selectively inhibits HIV-1 protease in cell-free systems. The finding that the fulleroid compounds of this invention demonstrate antiprotease activity in addition to virucidal properties suggests that a mechanism other than inhibition of reverse transcriptase is responsible for the inactivation of virus, and is consistent with the belief that the therapeutic efficacy of the compounds herein results primarily from their binding to HIVP.

Routine protocols can be followed to determine whether a derivatized buckministerfullerene compound has virucidal properties. For instance, to evaluate anti-HIVP activity, an assay with 0.1 M sodium acetate buffer, pH 5.5, at 37° C. and a concentration of recombinant HIVP enzyme of 0.08 $\mu$M can be incubated with the virus and the compound to be tested, varying the amount of the compound to determine the $IC_{50}$s concentration of the compound. This method is similar to that described by Ido, et al., *J. Biol. Chem.*, 266:24359–24366, 1991). Inhibition is time dependent, and preincubation with the inhibitor results in greater enzyme inhibition, indicating a slow binding process Cell culture evaluation techniques well known in the art can also be used to determine the antiviral and antivirucidal properties of the compounds of this invention. For instance about 200 50% tissue culture infective doses of the virus to be tested and 2 ml of the compound to be tested are incubated for 2 hours at 37° C. After incubation, a growth medium is added to each tube and the tube is centrifuged at about 40,000 rpm for 30 minutes at 4° C. The supernatant is removed and the virus pellet is resuspended in fresh medium. The virions are added to human PBMC that has been stimulated for 2 days with phytohemagglutinin in 25 $cm^2$ flasks in a total of 10 ml of growth medium. After about six days, residual virus in the supernatant are quantitated by an RT assay such as that described by R. F. Schinazi, et al., *Antimicrob. Agents Chemother.*, 36:2423–2431, 1992, or in *Current Protocols in Molecular Biology*, Ed. by F. M. Ausubel, Current Protocols, Vol. 1, §9.13.3 and in Example 8, Table 2 below.

The inherent problem with approaches aimed at inhibiting HIV and viral proteases is that the compounds must target the virion and penetrate the virus membrane or must be present in sufficient quantity near the cell membrane prior to virion budding to bind with the target compound. In addition, antiviral compounds such as protease inhibitors must be resistant to degradative enzyme, have a low protein binding affinity, and ideally should be orally bioavailable. These advantages are all provided by the buckminsterfullerene derivatives of this invention because the fullerene molecule itself is relatively inert as compared with peptides and many chemical entities.

Consequently, in one embodiment of the invention the water soluble derivatized compounds are used to inhibit human retroviral infections by contacting cells infected with a retrovirus, such as a strain of HIV, with a pharmaceutically effective amount of a compound of this invention. The contacting may be by any conventional means such as orally, by intravenous or parenteral injection, or by extracorporeal contact via a blood shunting device. The compounds of the invention may also be used as a prophylactic against infection by a human retrovirus, such as HIV. In prophylactic use a formulation containing an anti-viral effective amount of the antiviral compound, such as a contraceptive or lubricant, is applied topically to the area to be protected. In another embodiment of the invention, the buckministerfullerene compounds are used for antiviral or antivirucidal treatment and/or prophylaxis in combination with other known protease inhibitors and/or compounds known to be effective against HIV, such as AZT, DOC, D4T, 3TC and the like.

As used herein, a pharmaceutically effective amount of an antiviral compound is an amount calculated to achieve and maintain therapeutic blood levels in a human or animal over the period of time desired. As used herein an antiviral effective amount is one calculated to prevent viability of the virus upon contact with infected cells. A virucidal effective amount is one calculated to prevent viability of cell-free virus upon contact. These amounts vary with the potency of each compound, the amount required for the desired therapeutic or prophylactic effect, the rate of elimination or breakdown of the substance by the body once it has entered the bloodstream and the amount of the antiviral compound in the formulation. In accordance with conventional prudent formulating practices, a dosage near the lower end of the useful range of a particular agent is usually employed initially and the dosage increased or decreased as indicated from the observed response, as in the routine procedure of the physician. However, in general the dosage preferred for the compounds of this invention is sufficient to achieve a blood level of between 0.1 and 100 $\mu$M, preferably between about 1 and 25 $\mu$M.

The following examples illustrate the manner in which the invention can be practiced. It is understood, however, that the examples are for the purpose of illustration and the invention is not to be regarded as limited to any of the specific materials or conditions therein.

EXAMPLE 1

Modeling Complementarity of $C_{60}$ with the HIVP Active Site

To test the hypothesis regarding the complementarity of the $C_{60}$ with the HIVP active site, a model of $C_{60}$ was created and minimized using the SYBYL package (Version 5.4, Tripos Associates, Inc.). Atomic point charges were calculated using the Gasteiger-Huckel method. For conformationally, flexible ligands, torsions were initially set to anticipated low-energy conformers. Minimization to the used model structure was performed using the Maximin2 minimizer and Tripos force field and parameters. Docking to the active site of the studied protein was done using the program DOCK3. Grids required by DOCK3 were generated against the dimer formed from the Protein Data bank file 3hvp, using the standard AMBER united atom charges and van der Waals parameters. Single mode runs of modeled compounds against the active site of HIVP were performed using the following parameters: dislim=1.500, nodlim=5, ratiom=0.0000, lownod=4, lbinsz=0.4000, lovlap=0.1000, sbinsz=0.8000, and sovlap=0.2000. All molecular graphics were produced using the MIDAS Plus system (Available from University of California, San Francisco). Molecular surfaces were generated using the program MS, written by Michael Connolly, University of California, San Francisco, Calif.). A probe sphere diameter of 1.4 Å to minimize four water molecules on the surface of the protein, and default values for van der Waals radii were used.

The model produced had a diameter within 0.2 Å of the known diameter of 10 Å for $C_{60}$ as spectroscopically determined (S. Liu, supra). This model was fitted into the active site of the so-called "open" (i.e., uncomplexed) form of the HIVP using the program DOCK3, which finds optimal orientations of a ligand with its receptor, scoring on the basis of van der Waals contacts and complementary electrostatics. This procedure produced complexes with the $C_{60}$ squarely in the center of the active site, forming good van der Waals contacts with the active site surface, thereby reinforcing our model.

Figure 1B:
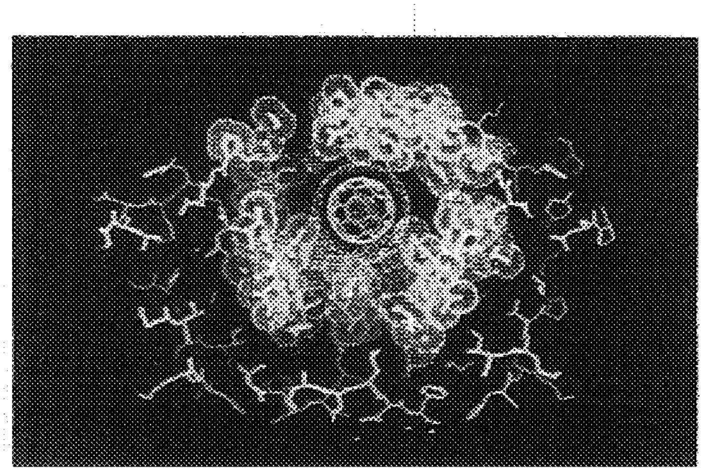
FIG. 1B shows the top scoring $C_{60}$ orientation from the same view as in FIG. 1A. The $C_{60}$ is colored magenta, and the van der Waals surface of the active site and ligand are shown.
Figure 1C:
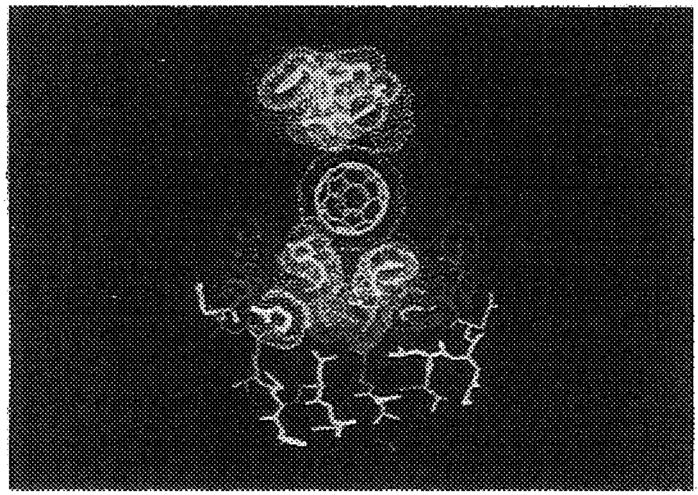
FIG. 1C shows a 90° cross section of the complex of FIG. 1B.

FIGS. 1B and 1C show the highest scoring complex of $C_{60}$ with HIVP in "front" and "side" views, which show the van der Waals surface contacts. The change in solvent-exposed surface upon binding was determined in order to approximate the maximum magnitude of hydrophobic interactions. This was accomplished by first determining the total surface area of the active site and $C_{60}$ molecules separately and then subtracting the total surface area of the highest scoring DOCK3 $C_{50}$ HIVP complex All surface areas were determined from molecular surfaces generated by the program MS. The calculation indicates that 298 $Å^2$ of primarily hydrophobic surface is removed from solvent exposure by complex formation. This total desolvated surface was further characterized by summing the individual surface elements according to atom type. The result of this summation (Table 2) is that the large majority (273 $Å^2$ or 92%) of the desolvated surface is due to $C_{60}$ carbon/HIVP carbon atom contact. The small amount of oxygen desolvation (7%) is due primarily to the partial blockage of the catalytic aspartates. Using the figure of 69.2 cal/(mol $Å^2$) recently shown to accurately describe the free energy released upon desolvation of hydrophobic molecular surface, (I. Tunon, et al., *Protein Eng*., 5:715–716, 1992), the calculated resultant free energy gain upon binding due to the carbon surface that is desolvated is 19 kcal/mol.

In order to estimate an approximate binding constant of a $C_{60}$ derivative, this value has to be corrected for the free energy cost due to loss of translational/rotational entropy that accompanies binding. This value has been estimated to be on the order of 7–11 kcal/mol. After this energetic cost is taken into account, the result is a total $\Delta G_{bind}$ of 8–12 kcal/mol. Converting this to $K_d$ values using the expression $\Delta G° = -RT \ln K_d$ results in dissociation constants on the order of $10^{-6}$–$10^{-9}$ M.

Several factors have been left out of this analysis, for example, rotational entropy persistence of the $C_{60}$ in the active site, conformational energy of the HIVP, and interaction of the catalytic aspartates with the $C_{60}$ surface. However, these values are all expected to be very small. The purpose of this analysis is to account for the factors influencing binding that are reasonably estimated from our understanding of protein-ligand interactions.

TABLE 2

Breakdown of Molecular Surface Changes upon $C_{60}$/HIVP Complexation According to Atom Type[a]

| Compound | C | N | O |
|---|---|---|---|
| Complex (HIVP + $C_{60}$) | 1537.64 | 109.272 | 266.456 |
| HIVP | 1402.55 | 112.504 | 287.898 |
| $C_{60}$ | 408.95 | 0 | 0 |
| Total Change ($Å^2$) | −273.31 | −3.232 | −21.442 |

[a]The surface areas of the complex and of HIVP were determined for an identical subset of the total protein structure which contained and flanked the active site.

EXAMPLE 2

Modeling Complementarity of a Water Soluble Derivative of $C_{60}$ with the HIVP Active Site (Compound 2c)

Figure 2:
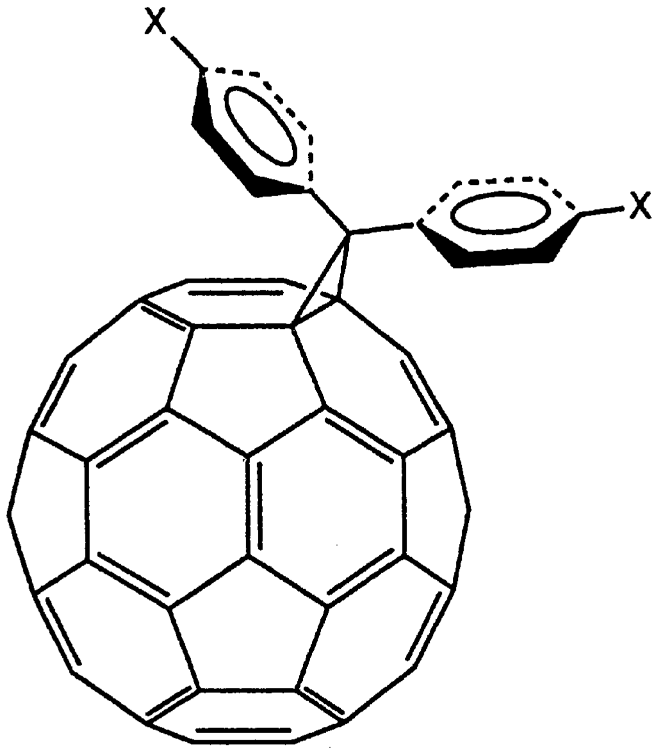
FIG. 2 shows compound 2c wherein X=$HOC(O)(CH_2)_2C(O)NH(CH_2)$.
Figure 3A:
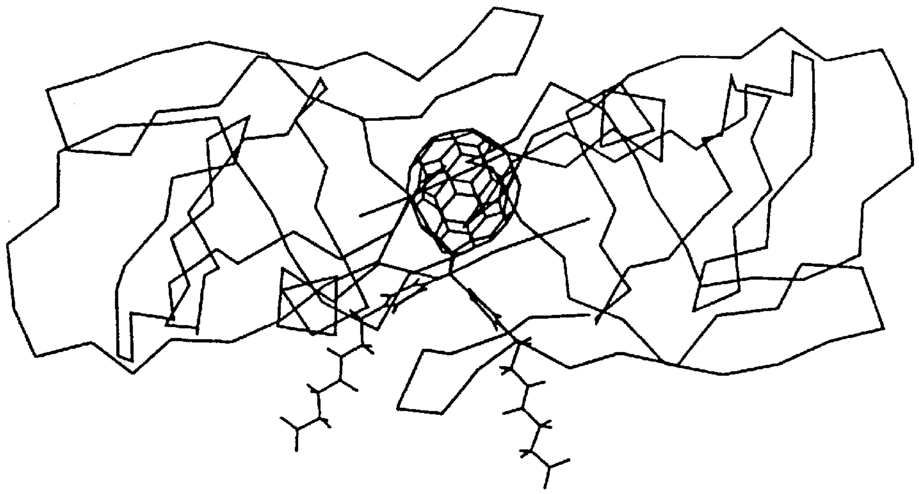
FIG. 3A shows the most favorable DOCK3 complex of compound 1 with the HIVP molecule in "front" view.
Figure 3B:
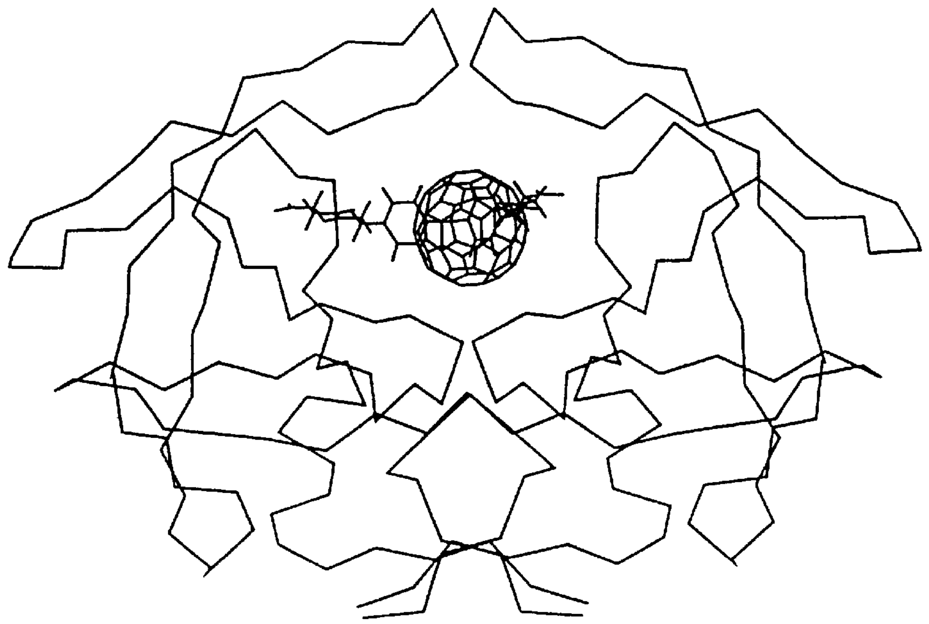
FIG. 3B shows the most favorable DOCK3 complex of compound 1 with the HIVP molecule in "top" view. For clarity, only the α-carbon chain trace of HIVP is shown.

A computer model of the complementarity of bis (phenethylamino-succinate) $C_{60}$ (compound 2c, FIG. 2), a relatively synthetically accessible water-soluble $C_{60}$ derivative, was generated using the computer programs and procedures described in EXAMPLE 1. The highest scoring DOCK3 complex of this compound with the HIVP again positions the core $C_{60}$ in the center of the active site, with the charged side chains extending through the mouth of the active site into solution as shown in FIG. 3.

EXAMPLE 3

Assay of Inhibition of HIV-1 Protease by Compound 2c

The ability of compound 2c to inhibit the HIVP was assayed with an HPLC method as described in R. L DesJarlais, et al., *Proc. Natl. Acad. Sci U.S*., 87:6644–6648, 1990. The $K_i$ value for compound 2c was found to be 5.3 μM (SE 0.98). Assays were performed in buffer containing 50 mM NaAc pH 5.5, 1.0 M NaCl, 5% glycerol, 1% DMSO, and 2 mM EDTA. Inhibitor was preincubated with ≈0.05 μg of enzyme for 5 minutes at which time the reaction was initiated by addition of substrate. The reaction was quenched at <15% product formation by the addition of 15 μL of 10% TFA. The cleavage products of the substrate peptide H-Lys-Ala-Arg-Val-Tyr-p-nitro-Phe-Glu-Alalle-NH2 (made by Bachem, Philadelphia, Pa.) were assayed by HPLC using a 10–40% (acetonitrile, 0.1% TFA):(water, 0.1% TFA) gradient over 30 minutes at 1 mL/minute. Product was quantitated by integration of peak areas followed by comparison to product standard curves.

Figure 4:
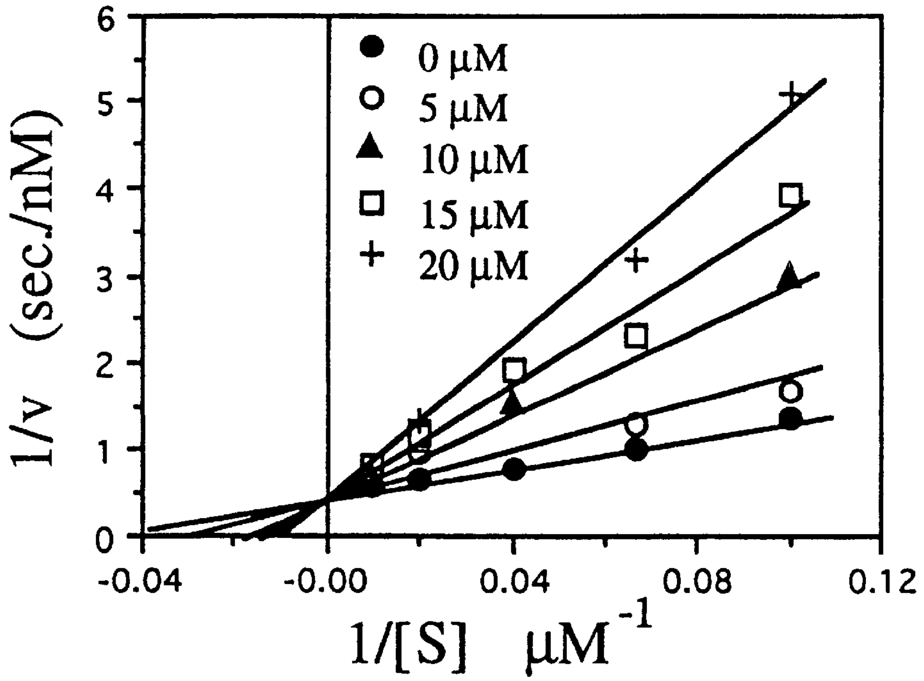
FIG. 4 shows a double reciprocal plot of inhibition of HIVP by compound 1. Standard errors are indicated in brackets.

Determination of kinetic constants was done with the program KinetAsyst (IntelliKinetics) by fitting of the data to the equation $v=V_mS/K_{m\infty}(1+I/K_i)+S]$ which describes competitive inhibition. $K_i\Delta$: 5.3 μM [SE 0.98]. $K_m$: 15.9 μM [2.9]. Vm: 1.9 nM/s [0.1]. As shown in FIG. 4, the kinetic data fit the pattern of competitive inhibition well. This supports the proposed model complex, as the predicted binding mode of the $C_{60}$ core should preclude any inhibitor binding while substrate is bound.

The parent compound to compound 2c, where $X=(CH_2)_2NH_2$, was tested using similar materials and methods and found to have a $K_i$ of ≈2 μM. This Insensitivity of binding to the nature of the $C_{60}$ side chain supports the predicted binding mode, which positions the side chains away from the active site into full solvent contact. It also predicts that the side chains can be selected to increase solubility of the $C_{60}$ derivative without adversely affecting the binding mode.

EXAMPLE 4

Figure 5:
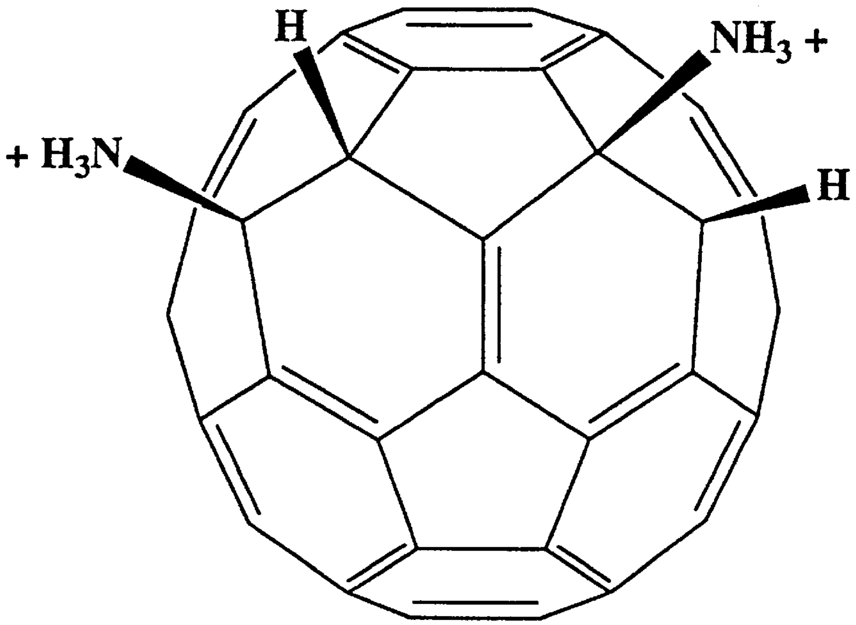
FIG. 5 is a schematic representation of compound 2.
Figure 6A:
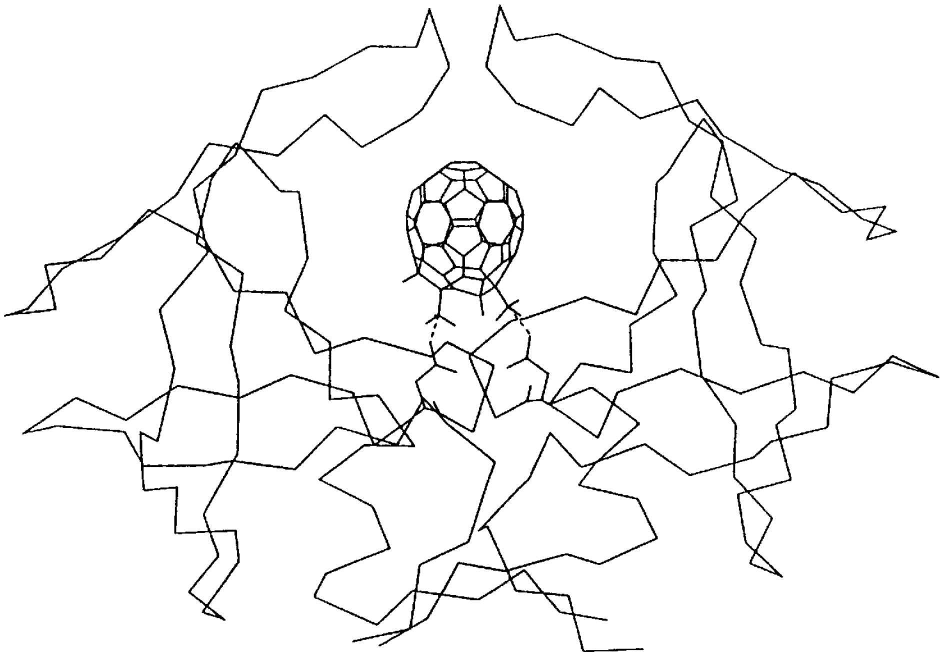
FIG. 6A shows the "front" view of the complex.
Figure 6B:
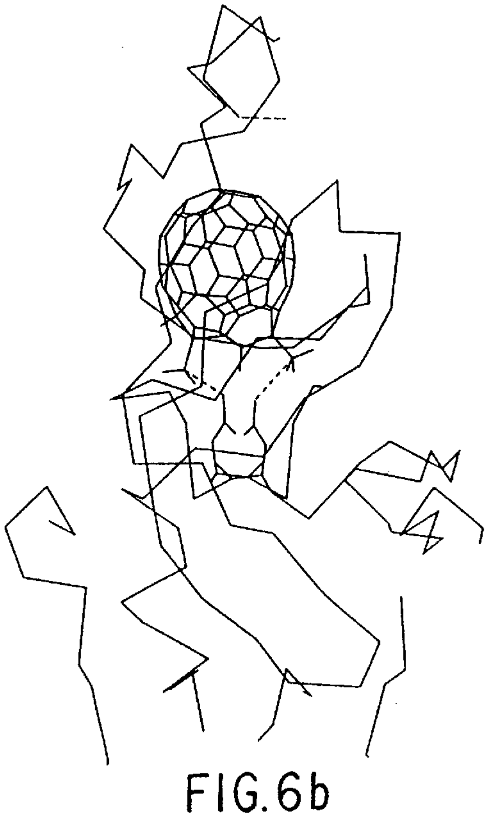
FIG. 6B shows the "side" view of the complex. Close approach of compound 2 amino groups and HIVP catalytic aspartate oxygens is highlighted with dashed lines. For clarity, only the catalytic aspartates and the α-carbon chain trace of HIVP are shown.

Modeling Complementarity of a Water Soluble Derivative of $C_{60}$ with the HIVP Active Site A computer model of the complementarity of 1,4-diamino $C_{60}$ (compound 2, FIG. 5), was generated using the computer programs and procedures described in EXAMPLE 1. As shown in FIG. 6, DOCK3 is able to orient the derivatized compound within the active site, placing the core $C_{60}$ in a similar position to that of compound 1, again allowing extensive nonpolar van der Waals surface interaction. In addition, the two amino groups effectively bridge the oxygens of the catalytic aspartates, approaching within 2.7 Å and 3.4 Å, respectively (N-O) distance), thus making these amino/carboxyl interactions good candidates for improving overall binding.

EXAMPLE 5

A. Preparation of N-Acetyl-2-pbenyethyhamine.

This compound was prepared from 2-phenylethylamine and acetic anhydride according to a procedure taught by M. E. Smith, et al, *J. Am. Chem. Soc.*, 50:657, 1938, to yield compound 1.

B. Preparation of 4,4'-Bis(N-acetyl-2-aminoethyl) benzophonone (1a).

Compound 1 (3.95 g, 24–2 mmol) was dissolved in $CCl_4$ (80 mL). The solution was cooled in an ice bath, 13.4 g (100 mmol) of $AlCl_3$ was added slowly, and the resulting slurry was stirred for 12 h at room temperature. The reaction mixture was poured into ice cold 2 N aqueous HCl, made basic with concentrated KOH solution, and extracted with $CH_2Cl_2$ (400 mL). The organic layer was evaporated, and the crude product was purified by column chromatography (silica, $CH_2Cl$/MeOH, 95:5 v/v). Yield: 3.7 g (82%). A sample was recrystallized from toluene/methanol and characterized as follows: mp 176–178° C.; HRMS m/z calculated for $C_{26}H_{24}N_2O_2$ 352.179, found 352.1823. $^1H$ NMR ($CDCl_3$: δ 7.73, 7.31 (2 d, 8H, J=8 Hz, arom H), 5.79 (br s, 2H, NH), 3.54 (m, 4H, $CH_2CH_2N$), 2.90 (t, 4H, $PhCH_2CH_2N$), 1.97 (s, 6H, $COCH_3$). IR (KBr): 3280 s, 3060 m, 2910–2850 m, 1635 s, 1545 s, 1280 s $cm^{-1}$.

C. Preparation of 4,4-Bis (N-acetyl-2-aminoethyl) benzophenone Hydrazone (1b).

Compound 2 (430 mg, 1.22 mmol) was dissolved in dry ethanol (70 mL). Dry hydrazine (3.5 mL) and acetic acid (7 mL) were added, and the reaction mixture was allowed to reflux for 1.5 h. The solvents were evaporated in vacuo, and the product was purified by column chromatography (neutral alumina, $CH_2Cl_2$/MeOH, 98:2 v/v). Yield: 290 mg (66%) as a glassy solid. $^1H$ NMR ($CDCl_3$: 7.1–7.43 (m, 8H, arom H), 5.72 and 5.57 (2 br s, 2H, NH), 3.4–3.65 (m, 4H, $CH_2CH_2N$), 2.70–2.95 (4H, $PhCH_2CH_2N$), 1.93 and 1.99 (2 s, 6H, $COCH_3$). HRMS (EI): m/z calcd 366.2056, found 366.2068.

D. Preparation of 4,4'-Bis(N-acetyl-2aminoethyl) diphenyldiazomethane (1c).

Hydrazone 1b (32 mg, 0.086 mmol) was dissolved in 20 mL of freshly distilled THF. One drop of a saturated solution of NaOH in EtOH and 51 mg of nickel peroxide were added. The mixture was stirred over molecular sieves (4 Å) until all the hydrazone had disappeared and one red spot was visible on TLC (1.5 h). The solution was filtered over a Celite pad and used directly for the next step. $^1H$ NMR ($CDCl_3$: 7.23 (s, 8H, arom H), 5.71 (br s, 2H, NH), 3.52 (m, 4H, $CH_2CH_2N$). 2.83 (4H, $PhCH_2CH_2N$), 1.96 (s, 6H, $COCH_3$). IR (neat): 3280, 3090, 2040, 1645, 1545, 1440, 1290 $cm^{-1}$. UV-vis (THF): 533, 288, 266 nm.

E. Preparation of 4,4-Bis(N-acetyl-2-aminoethyl) dipbenyl $C_{61}$ (2a).

To a solution of $C_{60}$ (100 mg, 0.139 mmol) in toluene (400 mL) was added a solution of compound 1 (50 mg, 0.137 mmol) in THF (70 mL). The mixture was stirred overnight. The solvent was removed, and the product was purified by column chromatography (silica, toluene/MeOH, 93:7 v/v). The purified product was heated for 16 h in refluxing o-dichlorobenzene. The solvent was removed in vacuo, and traces of solvent were removed by precipitation with methanol from a toluene/methanol solution. Yield: 55 mg (38%) of 2a (75% based on consumed $C_{60}$). $^1H$ NMR ($CDCl_3/CD_3OD$): 8.06, 7.34 (2 d, 8H, arom H). 6.72 (br s, 2H, NH), 3.48 (t, 4H, $CH_2CH_2N$), 2.87 (4H, $PhCH_2CH_2N$), 1.95 (s, 6H, $COCH_3$). IR (KBr): 3280 br, 2930 m, 1655 s, 1550 s, 1432 s, 1369 m, 1291 m, 1192 m, 598 w, 581 w, 568 w, 532 s $cm^{-1}$ FABMS (m-nitrobenzyl alcohol): m/z 1057 $(M+H)^+$, 720 ($C_{60}^+$). Anal. Calcd for $C_{81}H_{24}N_2O_2H_2O$: C, 90.49; H, 2.34; N, 2.60. Found: C, 90.93; H, 2.55; N, 2.39. 4,4'-Bis(2-aminoethyl)diphenyl $C_{61}$ (2b). A solution of 25.7 mg of compound 2a in acetic acid (7.5 mL) and concentrated aqueous HCl (2 mL) was allowed to reflux overnight. The solvent was evaporated in vacuo to afford the product as its bis(hydrochloride). Yield: 25.0 mg (98%). $^1H$ NMR ($CD_3OD/CS_2$): 8.21, 7.43 (2 d, 8H, arom H), 3.18 (t, 4H, $CH_2CH_2N$) 3.01 (4H, $PhCH_2CH_2N$). IR (KBr): 3400 br, 3020 m, 2915 m, 1608 s, 1505 s, 1468 s, 1430 s, 1385 m, 1320 w, 1245 w, 1190 m, 1180 sh, 1125 1090, 1020, 960, 900, 815 sh, 800, 748, 715, 615, 590 w, 580 w, 560 w, 530 s $cm^{-1}$. FABMS (m-nitrobenzyl alcohol): m/z 973 $(M+H)^+$, 720($C_{60}$+)

F. Preparation of Water-Soluble $C_{60}$ Derivative (2c).

To 25 mg of 2b, 2 HCl (0.024 mmol) was added 103 mg (1.02 mmol) of succinic anhydride in 10 mL of dry pyridine. The resulting red solution was stirred overnight. The reaction mixture was poured into 2 N aqueous HCl (100 mL) and centrifuged. The precipitate was washed twice with water and dissolved in 25 mL of 0.1 N aqueous NaOH. The solution was centrifuged to remove insoluble side products, and the supernatant was acidified with concentrated aqueous HCl. The resulting precipitate was centrifuged, washed with water and methanol, and finally dried in vacuo. Yield 25.7 mg (93%). $^1H$ NMR ($CD_3OD/CS_2$): 8.10, 7.36 (2 d, 8H, arom H), 3.44 (t, 4H, $CH_2CH_2N$), 2.86 (t, 4H, $PhCH_2CH_2N$), 2.55 and 2.43 (2 t. 8H, $COCH_2CH_2CO$). $^{13}C$ NMR (DMSO-$d_6$, 125 MHz): d 173.78, 170.78, 148.93, 145.73, 144.58, 144.52, 144.24, 144.09, 143.98, 143.60, 143.30, 142.36, 142.30, 141.66, 141.59, 139.97, 139.41, 137.13, 136.75, 130.94, 128.90, 79.37, 51.24, 34.87, 30.01, 29.14. IR (KBr): 3425 br, 2925 m. 1706 s, 1650 s, 1550, 1427, 1190, 590 m, 575 m, 557 m, 526 s $cm-^1$. UV-vis ($CS_2$/MeOH) λmax (nm): 363, 433 (diagnostic for cyclopropane). 500 (diagnostic for cyclopropane). Reprecipitation with acid from base produced the MS sample which was pure by HPLC (column, VIDAC, $C_{18}$ reverse phase; eluent, 10% MeOH/water; detector, variable wave length, λmax 370 nm; flow rate, 0.5 mL/minute; retention time, 2.9–3.1 minutes (depending on pyridine concentration); impurity retention time, 5.87 minutes). Minor impurities with a dissimilar retention time to that of 2c appear to be in the methanolic pyridine used for elution, as determined from a blank run (X100 gain). The pyridine salt in methanol shows no impurities within experimental error (machine integration, 100%).

EXAMPLE 6

Mass Spectrometry, Sample preparation

Samples were prepared by mixing approximately 100 μg of analyte in a methanol:$CS_2$ solution (2:1 by volume) with 300 pL of a 50 mmol/L 2,5-dihydroxybenzoic acid (Fluka Chemical Co., Buchs, Switzerland) matrix solution containing 0.1% trifluoroacetic acid (Mallinkrodt, St. Louis, Mo.) in methanol and 30 μL of a 60 mmol/L aqueous NaCl solution. The resulting solutions were sprayed as aerosols onto a rotating stainless steel probe tip for homogenous deposition.

Matrix-assisted laser desorption/ionization (MALDI) Fourier transform mass spectra (FTMS) (D. L DeCamp, et al., *J. Med. Chem.*, 35:3426–3428, 1992) were obtained with 357-nm radiation from a Lambda Physik (Götingen, Germany) FL-2001 dye laser, pumped by a Lambda Physik EMG-201-MSC excimer laser (operating at 308 nm, 180 mJ/28 ns pulse) and a Millipore Extrel (Madison, Wis.) FTMS-2000 dual cell spectrometer equipped with a 7-T superconducting magnet. Spectra were obtained using a gated trapping sequence (DeCamp, supra; C. Köster, *J. Am. Chem. Soc.*, 114:7572–7574, 1992) with ejection of ions below m/z 750 and a 200-V peak-to peak chirp excitation from 1 to 200 kHz at 180 Hz/μs sweep rate followed by detection. Each spectrum resulted from averaging between 2 and 27 time domain scans, acquiring 65,536 data points per scan. The averaged time domain data were augmented by an equal number of zeroes and base-line corrected prior to magnitude mode Fourier transformation. No anodization was used. Polyethyleneglycol-1000 was used as an external celebrant for the full spectra. Accurate mass measurements of molecular ion species were made by adding a small quantity of an internal celebrant to the sample solutions prior to deposition on the sample probe. Polyethyleneglycol-1000 served as an internal celebrant (9-point calibration) for $[M^+Na]^+$ mass determination, and 2,4,6-tris (perfluoroheptyl)-1,3,5triazine (Fluka Chemical, Buchs, Switzerland) was used as an internal celebrant (2-point calibration, M− and [M−F]−) for analyte M− mass determinations.

EXAMPLE 7

High-Resolution Mass Spectra

Figure 7:
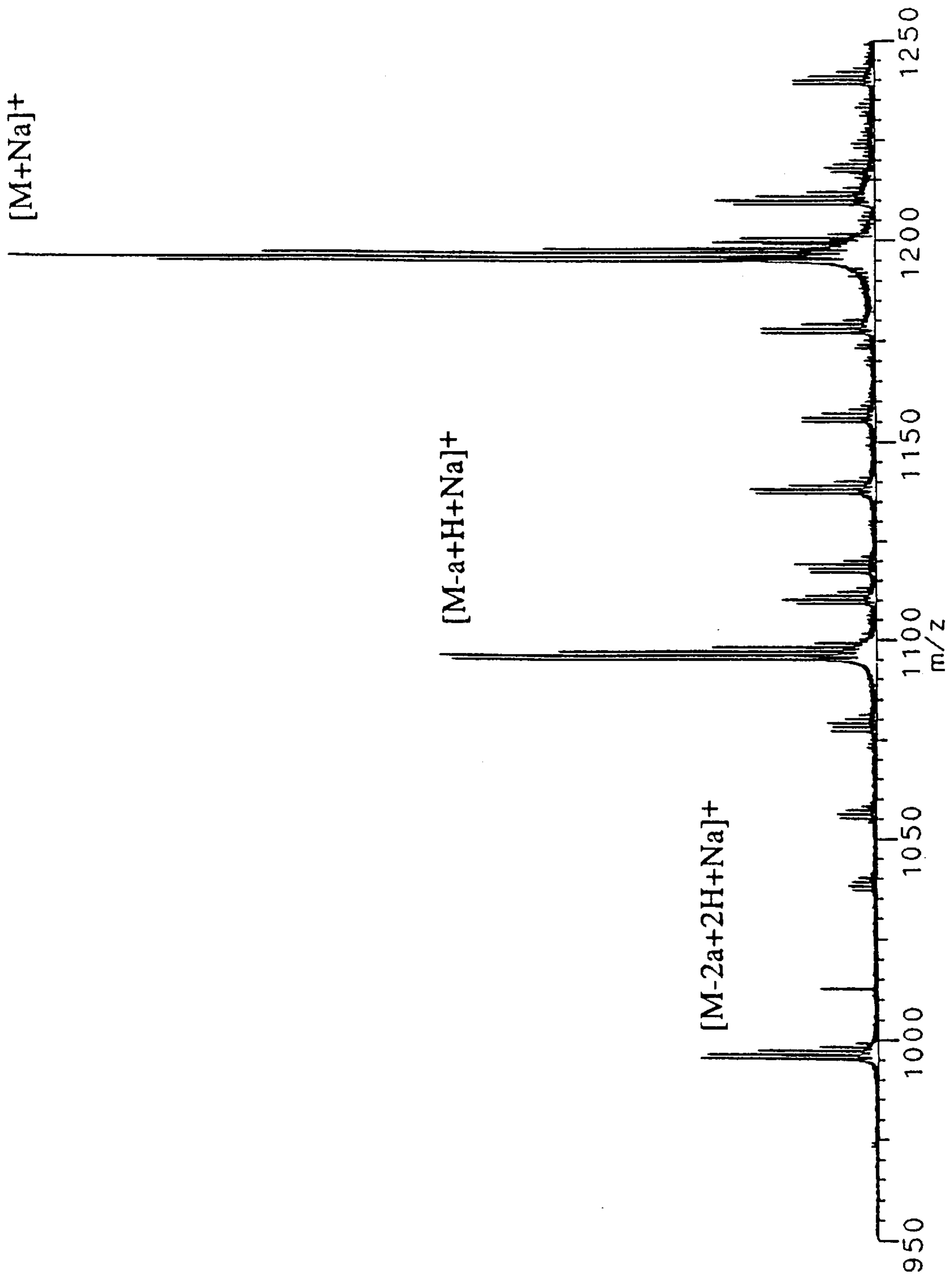
FIG. 7 is a graph showing the high-resolution positive ion MALDI Fourier transform mass spectrum of 2c, where a=$COCH_2CH_2COOH$.
Figure 8:
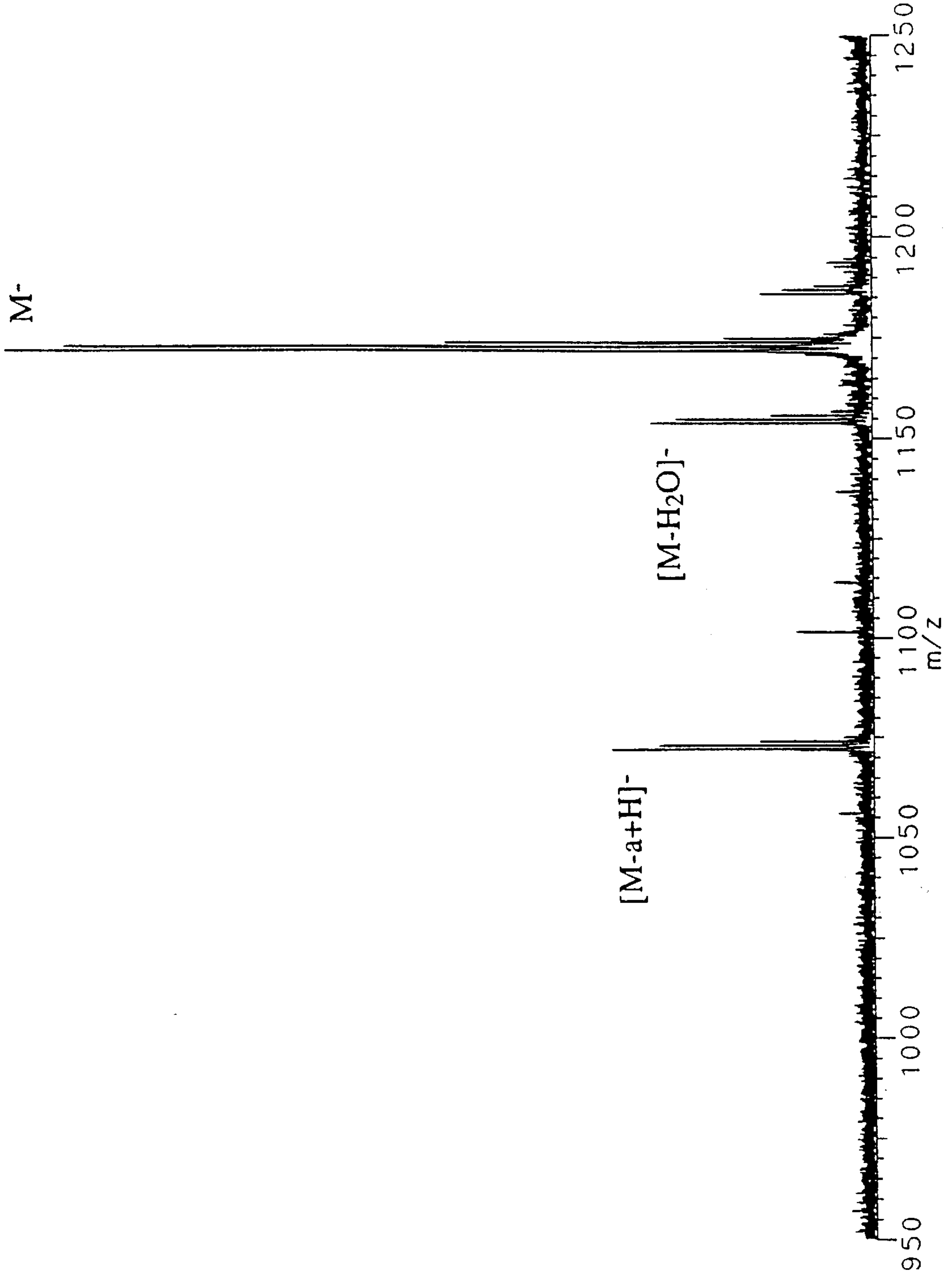
FIG. 8 is a graph showing the high-resolution negative ion MALDI Fourier transform mass spectrum of 2c, where a=$COCH_2CH_2COOH$.

FIG. 7 contains the high resolution MALDI-FTMS (matrix-assisted laser desorption/ionization Fourier transform mass spectra) (J. A. Castoro, et al., *Rapid Commun. Mass Spectrum.*, 6:239–241, 1992) positive ion spectrum of compound 2c. As expected, almost all of the ions observed are sodium attachment ions. The most abundant ion is the molecular sodium attachment ion $[M+Na]^+$, with m/z 1195.2. The second and third most abundant ions correspond to loss of either one or two $-COCH_2CH_2COOH$ groups. Similarly, the most abundant ion in the negative ion spectrum (FIG. 8) is the M− ion, with m/z 1171.8. The other two most abundant ions correspond to loss of $H_2O$ and loss of a $-COCH_2CH_2COOH$ fragment. Mass resolution of approximately 8000 is obtained for the positive ion spectrum and resolution of about 9000 for the negative ion spectrum.

Figure 9B:
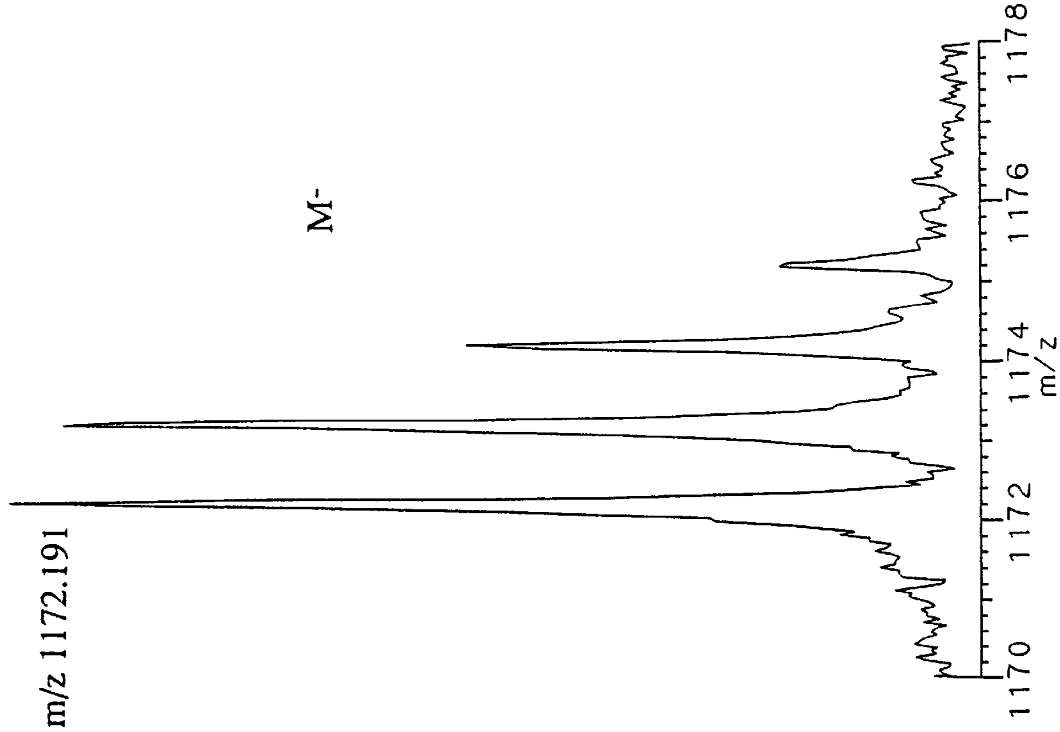
FIG. 9B shows measurements using $M^{-}$, 2,4,6-tris(perfluoroheptyl)-1,3,5-triazine as internal celebrant.
Figure 9A:
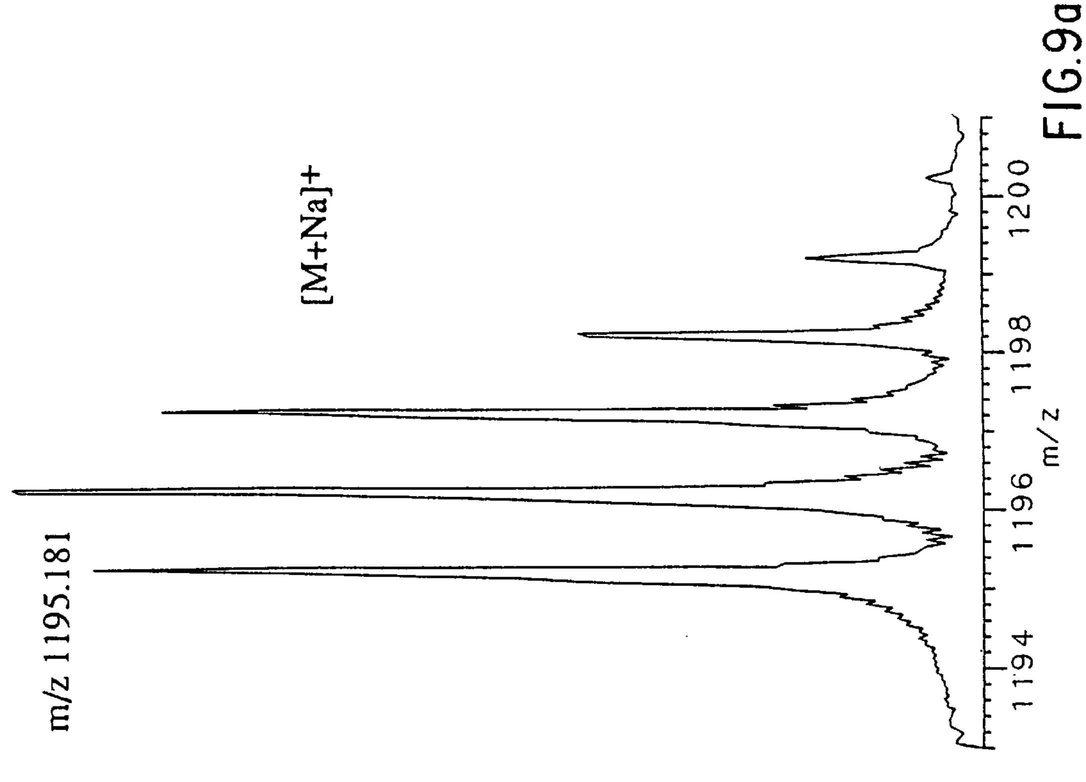
FIG. 9A shows measurements using $[M^{+}Na]^{+}$, polyethyleneglycol-1000 as internal celebrant.

In another set of measurements, with the appropriate internal calibrants added, an average mass measurement difference of 2.1 ppm from the calculated mass of the all $^{12}C$ molecular ion species $[M+Na]^+$ was measured for four separate spectra, each obtained by averaging the spectra resulting from nine laser shots. For the negative molecular ion, M−, an average mass accuracy of 7.1 ppm was obtained from all the $^{12}C$ ions determined from three spectra, each resulting from time domain addition of 27 spectra acquired using the corresponding number of laser shots. FIGS. 9A and 9B show typical mass measurement accuracy results for the molecular ion region of the positive and negative ion spectra. No peaks attributable to $C_{60}$ ions were seen in either positive or negative ion MALDI spectra.

EXAMPLE 8

Assays of Antiviral Activity

Compound 2c was evaluated for antiviral activity in cells acutely and chronically infected with human immunodeficiency virus (HIV). The results are shown in TABLE 3 below. Reverse transcriptase (RT) levels associated with virus were determined with virus concentrated from cell culture supernatants by high-speed centrifugation to reduce the chances of drug carryover in the enzyme assay using the method described in R. F. Schinazi, et al., *Antimicrob. Agents Chemother.*, 36:2423–2431, 1992. In human peripheral blood mononuclear cells (PBMC) infected with HIV type $1_{LAI}$ (HIV-$1_{LAI}$), compound 2c demonstrated activity with a median effective concentration ($EC_{50}$) (mean±standard deviation) of 7.3±5.9 μM. Surprisingly, this water-soluble fulleroid was also found to be effective in chronically infected H9 cells, with an $EC_{50}$ of 10.8±8.2 μM. Compound 2c appeared to be effective in human PBMC acutely infected with HIV-$2_{ROD}$, with an $EC_{50}$ of 5.5±3.8 μM. As shown by the data in TABLE 3,3'-Azido-3'-deoxythymidine (AZT) used as a positive control had significant activity against HIV-1 and HIV-2 in acutely infected cells but no effect in chronically infected H9 cells. However, in acutely infected cells, AZT was markedly more potent than compound 2c.

To determine whether the fullerene may bind tightly to inactivate the viral RT, we also measured levels of HIV-1 p24 in supernatants of treated and untreated cultures. Clarified supernatants were treated with Triton X-100 (Sigma Chemicals, St. Louis, Mo.) and tested for HIV-1 antigen by immunocapture with a commercial kit (Abbott, North Chicago, Ill.). In PBMC acutely infected with HIV-1, the mean $EC_{50}$ increased from 7.3 μM in an RT assay to 50 μM in a p24 assay, suggesting virus inactivation as the primary antiviral mechanism for this compound.

To confirm these findings, inactivation studies with HIV-$1_{LAI}$ were performed. Briefly, in a Nalgene (Rochester, N.Y.) tube, 75 μl of virus (approximately 200 50% tissue culture infective doses) and 2 ml of compound 2c (5 to 25 μM) or medium without drug were incubated for 2 hours at 37° C. After incubation, 3 ml of RPMI 1640 growth medium (GIBCO/BRL, Grand Island, N.Y.) was added to each tube. Each tube was then centrifuged at 40,000 rpm for 30 minutes at 4° C. in a Beckman (Columbia, Md.) 70.1 Ti rotor. The supernatant was then removed, and the virus pellet was resuspended in fresh medium. The virions were added to human PBMC that had been stimulated for 2 days with phytohemagglutinin in 25-cm² flasks in a total of 10 ml of growth medium. On day 6, residual virus in the supernatant was quantitated by an RT assay, as described previously (R. F. Schinazi, et al., *Antimicrob. Agents Chemother.*, 36:2423–2431, 1992). Untreated virus-infected control had a mean RT activity of 1,140 kdpm per ml. When cell-free HIV-1 was incubated for 2 hours with compound 2c and the virus was concentrated and inoculated into fresh mitogen-stimulated human PBMC as described above, virus infectivity was reduced by more than 95% relative to that of the untreated control at 5 to 25 $\mu$M.

One of the well known problems in developing treatments for HIV is that development of single agents to treat HIV-1 infections inevitably results in the emergence of drug-resistant virus. The availability of AZT-resistant and -susceptible viruses allowed us to evaluate the compounds of this invention for their susceptibilities to these viruses in acutely infected PBMC in two experiments. The susceptibility of the pretherapy isolate (HIV-$1_{H112-2}$) ($EC_{50}$, 2–8 $\mu$M) to compound 2c was compared with that of the post-therapy AZT-resistant virus (HIV-$1_{G910-6}$) ($EC_{50}$, 2.8 $\mu$M) in lymphocytes. For this virus pair, the AZT $EC_{50}$s increased more than 180-fold, from ≦0.001 to 0.18 $\mu$M. For these results, the variance from the means was less than 15%. With nevirapine (BI-RG587)-resistant and -susceptible HIV-1 (D. D. Richman, et al., *AIDS Res. Hum. Retroviruses*, 8:1065–1071, 1992), the $EC_{50}$ for compound 2c increased from 0.53 to 8.7 $\mu$M, respectively, a 16-fold increase in resistance. In the same assay, the EC50 for TIBO [(+)-(5s)-4,5,6,7-tetrahydro-5methyl-6-(3-methyl-2-butenyl)imidazo (4,5,1-jk)(1,4)benzodiazepin-2(1H)-thione] R82150 increased >500-fold (data not shown).

An additional compound, a water-soluble histimid derivative of $C_{60}$ (Compound K of Table 1) was tested using the procedures described above and was found to have an $EC_{50}$ of 2.7 $\mu$M as determined in acutely infected cells.

TABLE 3

Summary of the Activities of Compound 2c. Phosphonoformate, and AZT

| | Antiviral Activity ($EC_{50}$ [$\mu$M]) in: | | |
|---|---|---|---|
| Compound | PBMC infected with $HIV_{LAI}$[b] | PBMC infected with HIV-$2_{ROD}$[b] | H9 cells infected with HIV-$1_{III}$[c] |
| 2c | 7.3 | 5.5 | 10.8 |
| PFA[e] | 0.43 | 0.44 | ND[f] |
| AZT[g] | 0.004 | 0.003 | >100 |

| | Cytotoxicity ($IC_{50}$ [$\mu$M])[a] in: | | | |
|---|---|---|---|---|
| Compound | PBMC | H9 Cells | Vero Cells (at day 3) | CEM cells |
| 2c | >100[d] | >100 | >100 | >100 |
| PFA[e] | >640 | ND | >100 | >100 |
| AZT[g] | >100 | 60 | 23 | 13 |

| | $IC_{50}$ Polymerases ($\mu$M) in: | |
|---|---|---|
| Compound | HIV-1 RT | DNA Polymerase$_\alpha$ |
| 2c | 4.6 | 4.9 |
| PFA[e] | 0.32 | >100 |
| AZT[g] | 0.04 | >100 |

[a]Measured by cell counts on day 6, except where indicated.
[b]Acutely infected. The virus RT level was determined on day 6 after infection. Values are means of quadruplicate experiments. The correlation coefficient for the data was >0.96. The variance from the means was less than 20%.
[c]Chronically-infected. The virus RT level was determined after 6 days of treatment. Values are means of duplicate experiments.
[d]Measured by radiolabeled thymidine uptake on day 2 and by cell counts on day 6.
[e]PFA, phosphonoformate.
[f]ND, not determined.
[g]AZT-5'-triphosphate was used for the enzyme assays.

The lack of cross-resistance with AZT suggests that combination of the fullerenes with AZT could have beneficial therapeutic effect. No cytotoxicity was demonstrable with compound 2c in uninfected, slowly dividing PBMC or rapidly dividing H9, Vero, or CEM cells. Few compounds have demonstrated selective antiviral activity in chronically infected cells (R. F. Schinazi, et al., *AIDS Res. Hum. Retroviruses*, 8:553–579, 1992). The apparent activity of compound 2c in acutely infected cells is comparable to that of the recently reported TAT inhibitor Ro 5-3335 developed by the Hoffmann LaRoche Co. (M. Hsu, et al., *Biochem. Soc. Trans.*, 20:525–531, 1992). However, it is highly likely that residual drug may inactivate the virus directly, resulting in an overestimation of the potency of the fulleroid in chronically infected H9 cells.

The compound was also evaluated for its inhibitory effect on recombinant p66/51 HIV-1 RT by using poly$(rA)_n$.oligo $(T)_{12-18}$ as the template-primer as described in Schinazi, et al. (1992, supra). Compound 2c was active against this enzyme, with a median inhibitory concentration ($IC_{50}$) of 4.6 $\mu$M. This value was of the same order of magnitude as that noted for the antiviral assays (TABLE 3). The compound did not demonstrate selectivity against cellular DNA polymerase α. The finding that compound 2c inhibits DNA polymerase a in a cell-free system with an $IC_{50}$ of 4.9 $\mu$M and also exhibits no cytotoxicity in various cells is consistent with the proposed virucidal mechanism, since one would anticipate some cytotoxicity if the compound were transported intracellularly. AZT-5' triphosphate and phosphonoformate (PFA), used as positive controls, were effective and selective against HIV-1 RT.

Compound 2c also has antiprotease activity. In an assay with 0.1 M sodium acetate buffer, pH 5.5, at 37° C. and an enzyme concentration of 0.08 $\mu$M, compound was found to have $IC_{50}$s of 2.0 $\mu$M against recombinant HIV-1 protease and 20 $\mu$M against pepsin (with 0.028 $\mu$M enzyme in 0.2 M sodium citrate, pH 2.0, at 37° C.). The method used for the assay was similar to that described by Ido, et al., *J. Biol. Chem.*, 266:24359–24366, 1991). Inhibition was time dependent, and preincubation with the inhibitor resulted in greater enzyme inhibition, indicating a slow binding process (data not shown).

EXAMPLE 9

Figure 10A:
FIG. 10A is a computer model of the active site of HIVP, showing that the active site does not have a perfectly circular cross section, but rather is oval.
Figure 10B:
FIG. 10B is a computer model of the complex of $C_{60}$ with the HIVP, showing that the complex leaves solvated surface area on either side of the core $C_{60}$.

Comparison of the computer models of the open and closed configuration of the HIVP molecule, shown in FIGS. 10A and 10B, respectively, reveal that upon complex formation with $C_{60}$, there are still gaps on either side of the fullerene that could be filled with non-polar groups, thereby improving binding by further decreasing solvated surface area. Further compounds B through F designed to achieve this goal were tested using the computer modeling protocol described above to determine the amount of energy released upon complex formation with the active site of HIVP. As can be seen in Table 4 below, as compared with compound 2c these derivatives all exhibited a greater change in salvation, suggesting they would have substantially improved binding.

TABLE 4
A
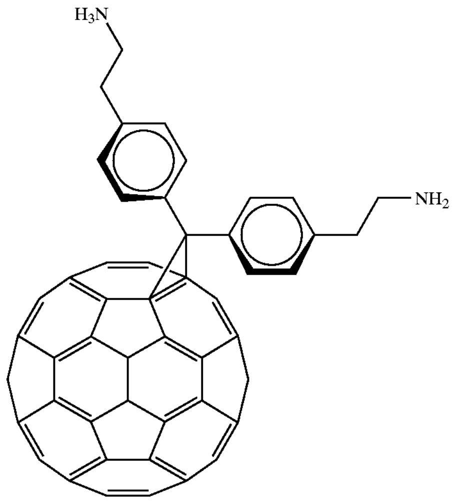
| Complex | Carbon | Nitrogen | Oxygen |
|---|---|---|---|
| Ligand | 1595.9 | 133.7 | 265 |
| Protein | 574.3 | 32.5 | 0 |
| TOTAL CHANGE | 1402.6 | 112.5 | 287.9 |
| Å$^2$ | −381.0 | −11.3 | −22.9 |
B
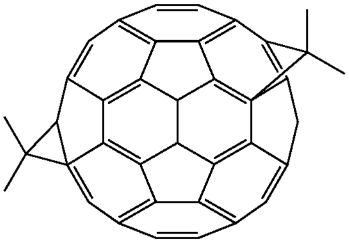
| Complex | Carbon | Nitrogen | Oxygen |
|---|---|---|---|
| Ligand | 1390.2 | 109.8 | 248 |
| Protein | 452 | 0 | 0 |
| TOTAL CHANGE | 1402.6 | 112.5 | 287.9 |
| Å$^2$ | −464.4 | −2.7 | −39.1 |
C
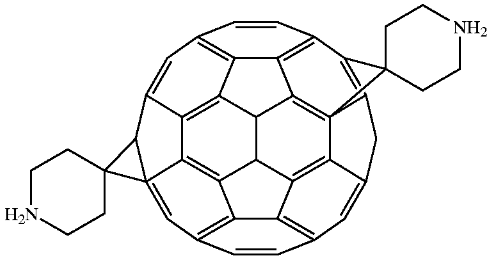
| Complex | Carbon | Nitrogen | Oxygen |
|---|---|---|---|
| Ligand | 1430.0 | 110.6 | 260.9 |
| Protein | 485.2 | 16 | 0 |
| TOTAL CHANGE | 1402.6 | 112.5 | 287.9 |
| Å$^2$ | −457.8 | −17.9 | −27.0 |
D
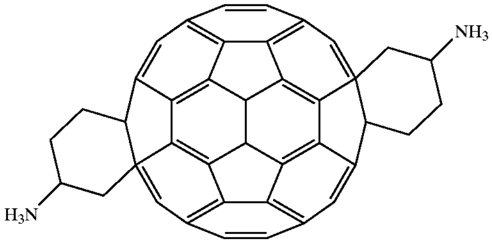
| Complex | Carbon | Nitrogen | Oxygen |
|---|---|---|---|
| Ligand | 1425.4 | 127.5 | 266.3 |
| Protein | 461.5 | 30.2 | 0 |
| TOTAL CHANGE | 1402.6 | 112.5 | 287.9 |
| Å$^2$ | −438.5 | −15.2 | −21.6 |

TABLE 4-continued

E

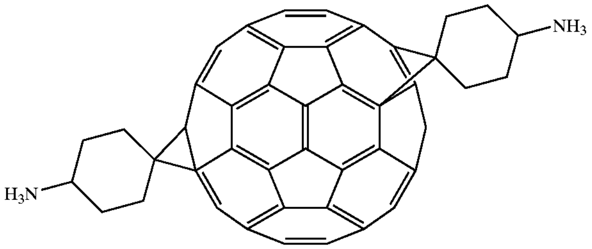

| Complex | Carbon | Nitrogen | Oxygen |
|---|---|---|---|
| Ligand | 1502.2 | 129.4 | 267.4 |
| Protein | 511.7 | 30.2 | 0 |
| TOTAL CHANGE | 1402.6 | 112.5 | 287.9 |
| Å$^2$ | −412.1 | −13.3 | −20.5 |

F

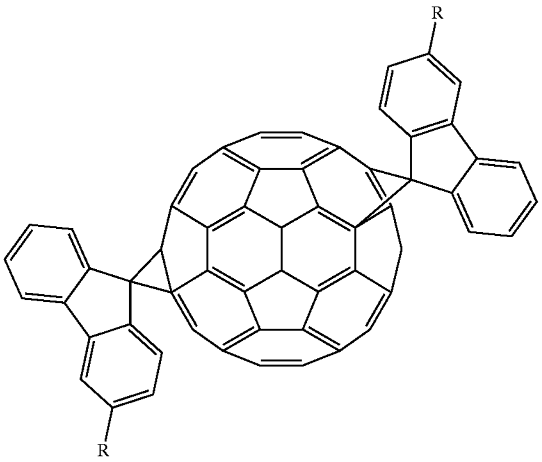

| Complex | Carbon | Nitrogen | Oxygen |
|---|---|---|---|
| Ligand | 1529.2 | 100.1 | 257.6 |
| Protein | 637.0 | 0 | 0 |
| TOTAL CHANGE | 1402.6 | 112.5 | 287.9 |
| Å$^2$ | −510.1 | −12.4 | −30.3 |

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. A method for identifying a fullerene compound that inactivates HIV protease comprising:

a) establishing a model of the HIVP molecule having an open active site containing $Asp_{25}$ and $Asp_{125}$;

b) establishing a model of a fullerene derivative symmetrically substituted with a polar organic moiety containing from 1 to 20 carbon atoms;

c) comparing the fit of the fullerene model with the active site of the HIV protease model to determine binding therebetween.

2. The method of claim 1 wherein the models are three-dimensional computer models and the comparing calculates a release of energy upon binding.

3. The method of claim 1 wherein the computer models are based upon x-ray diffraction solution of the crystal structures of HIVP and buckminsterfullerene.

4. The method of claim 3 wherein binding is determined by release of energy of at least 8 kcals/mol.

5. The method of claim 1 wherein the models are three-dimensional computer models and the comparing calculates a substantial reduction in solvated surface area upon binding.

6. The method of claim 1 wherein binding is between the $Asp_{25}$ and $Asp_{125}$ in the active site and the fullerene.

7. The method of claim 1 wherein the fullerene has the formula 4,4'-Bis(X) diphenyl $C_{61}$, wherein X is a polar organic moiety containing from 1 to 20 carbon atoms.

8. The method of claim 1 wherein the fullerene is a methanofullerene.

9. A method wherein the water soluble of claim 1 buckminsterfullerene or salt thereof selected from one or more of the following structures:

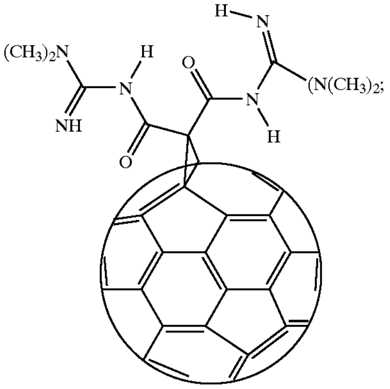

-continued
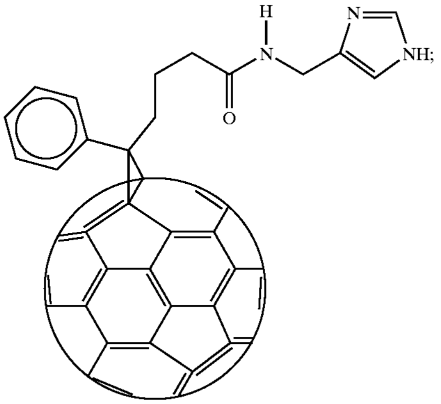
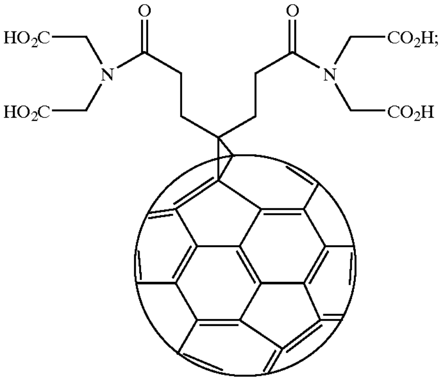
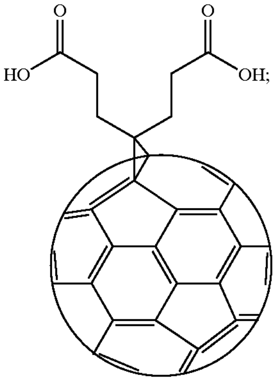
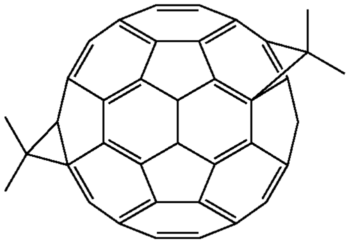
;
-continued
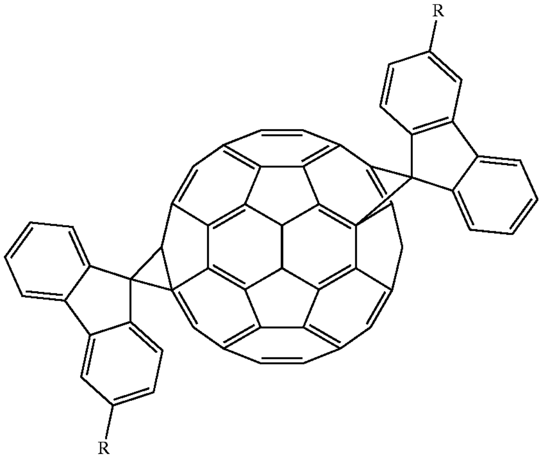
;
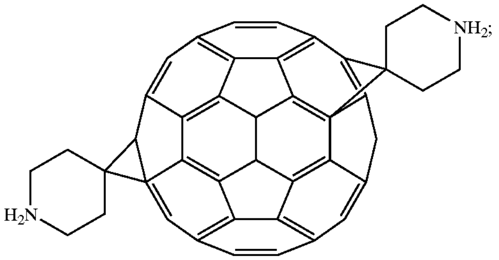
and
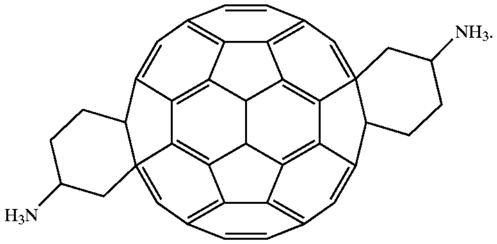
where R is an organic moiety of 1 to 10 carbon atoms.
10. The method of claim 9 wherein the buckminsterfullerene is a methanofullerene selected from the groups consisting of
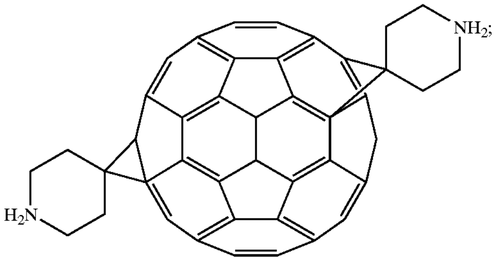
and
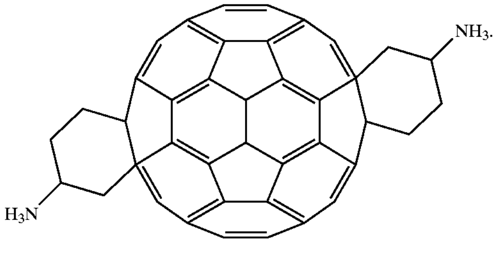

11. The method of claim 9 wherein the buckminsterfullerene is a methanofullerene of the structure

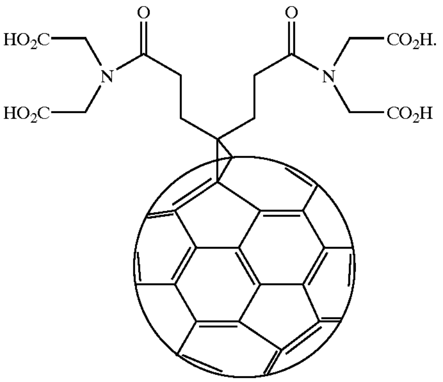

12. The method of claim 9 wherein the buckminsterfullerene is a methanofullerene selected from the groups consisting of

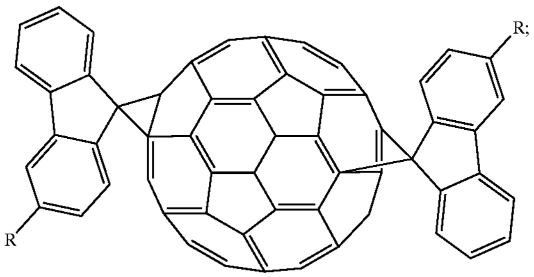 and

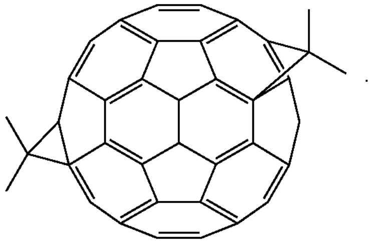

13. The method of claim 9 wherein the compound is the compound selected from the group consisting of

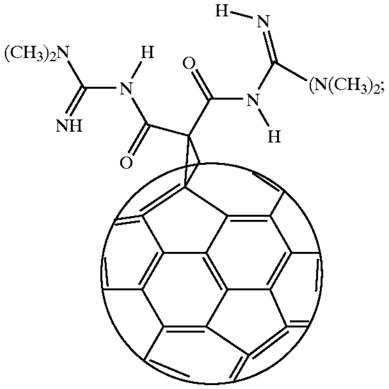

-continued

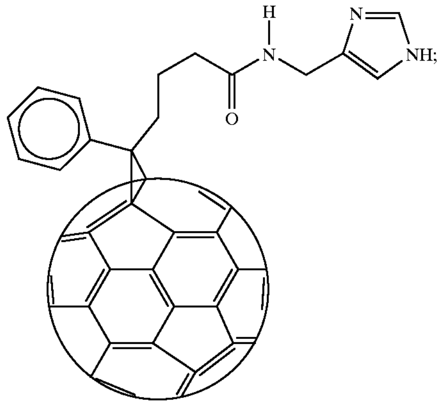 and

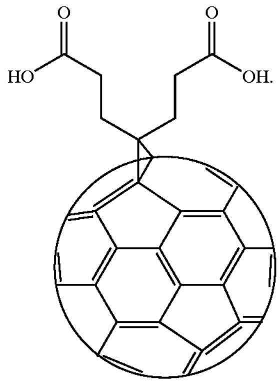

14. The method of claim 9 wherein the compound is a compound selected from the group consisting of

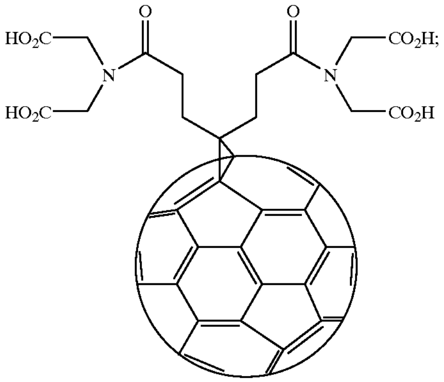 and

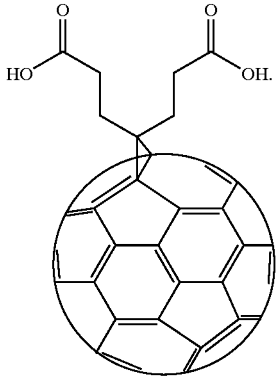

15. The method of claim 3 comprising a water soluble buckminsterfullerene, or a salt thereof selected from the group consisting of
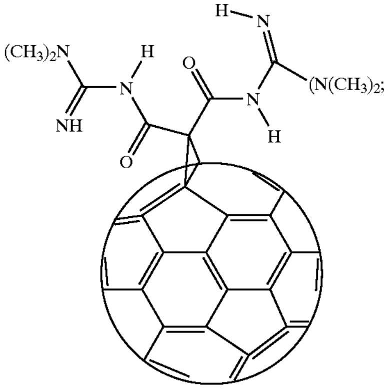
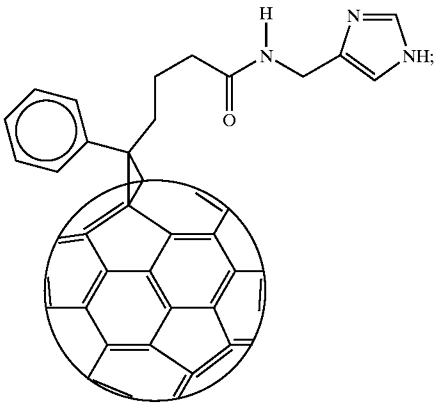
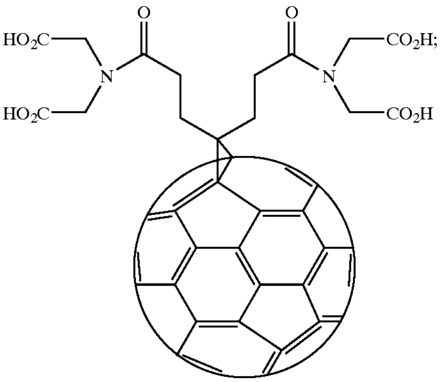
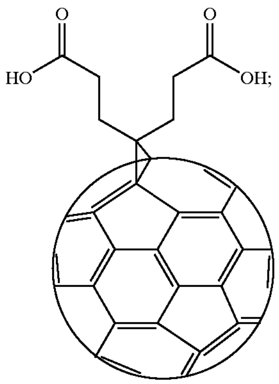
-continued
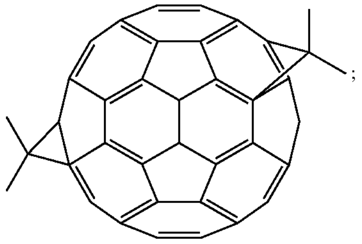
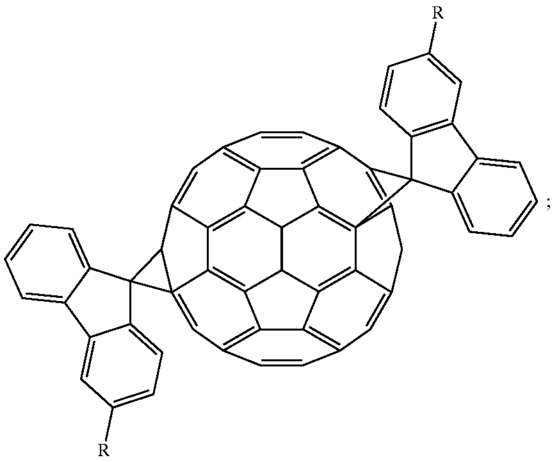
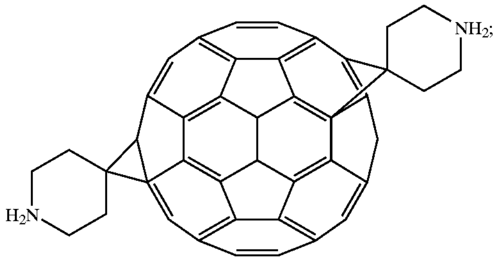
and
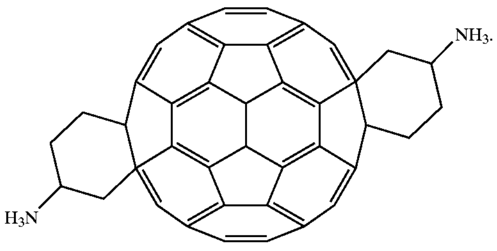
* * * * *